US010307406B2

(12) United States Patent
Lieberman et al.

(10) Patent No.: US 10,307,406 B2
(45) Date of Patent: Jun. 4, 2019

(54) METHODS AND COMPOSITIONS FOR RE-ACTIVATING EPSTEIN-BARR VIRUS AND SCREENING COMPOUNDS THEREFOR

(71) Applicants: The Wistar Institute of Anatomy and Biology, Philadelphia, PA (US); Drexel University, Philadelphia, PA (US)

(72) Inventors: Paul M. Lieberman, Wynnewood, PA (US); Nadezhda Tikhmyanova-Eckert, Cheltenham, PA (US); Joseph M. Salvino, Chester Springs, PA (US)

(73) Assignees: The Wistar Institute of Anatomy and Biology, Philadelphia, PA (US); Drexel University, Philadelphia, PA (US)

(*) Notice: Subject to any disclaimer, the term of this patent is extended or adjusted under 35 U.S.C. 154(b) by 0 days.

(21) Appl. No.: 14/912,949

(22) PCT Filed: Aug. 29, 2014

(86) PCT No.: PCT/US2014/053415
§ 371 (c)(1),
(2) Date: Feb. 19, 2016

(87) PCT Pub. No.: WO2015/031759
PCT Pub. Date: Mar. 5, 2015

(65) Prior Publication Data
US 2016/0206601 A1    Jul. 21, 2016

Related U.S. Application Data

(60) Provisional application No. 61/872,673, filed on Aug. 31, 2013.

(51) Int. Cl.
| A61K 31/437 | (2006.01) |
| C07D 471/04 | (2006.01) |
| A61K 31/19 | (2006.01) |
| A61K 31/522 | (2006.01) |
| A61K 31/69 | (2006.01) |
| A61K 45/06 | (2006.01) |
| C12Q 1/02 | (2006.01) |

(52) U.S. Cl.
CPC ............ *A61K 31/437* (2013.01); *A61K 31/19* (2013.01); *A61K 31/522* (2013.01); *A61K 31/69* (2013.01); *A61K 45/06* (2013.01); *C07D 471/04* (2013.01); *C12Q 1/025* (2013.01)

(58) Field of Classification Search
None
See application file for complete search history.

(56) References Cited

U.S. PATENT DOCUMENTS

| 6,933,313 B2 | 8/2005 | Harper et al. | |
| 2004/0132817 A1* | 7/2004 | Finzer ............... | A61K 31/00 514/557 |
| 2005/0282849 A1* | 12/2005 | Moon ............... | A61K 31/337 514/291 |
| 2010/0158858 A1 | 6/2010 | Cao et al. | |
| 2010/0233166 A1 | 9/2010 | Prendergast et al. | |
| 2012/0157400 A1 | 6/2012 | Cao et al. | |

FOREIGN PATENT DOCUMENTS

WO    WO-2005/089764    9/2005

OTHER PUBLICATIONS

Prayitno (Journal of Carcinogensis, 2006, 5, 1-4) (Year: 2006).*
International Preliminary Report on Patentability dated Mar. 10, 2016 in corresponding International Patent Application No. PCT/US2014/053415, filed Aug. 31, 2013.
Sugden, B. et al., A Vector That Replicates as a Plasmid and Can Be Efficiently Selected in B-Lymphoblasts Transformed by Epstein-Barr Virus, Molecular and Cellular Biology, Feb. 1985, 5(2): 410-413.
Amon, W. et al., Lytic Cycle Gene Regulation of Epstein-Barr Virus, Journal of Virology, Dec. 2004, 78(24): 13460-13469.
Davie, J. R. et al., Inhibition of Histone Deacetylase Activity by Butyrate, The Journal of Nutrition, Jul. 2003, 133(7): 2485S-2493S.
Rennekamp, A.J. et al., Initiation of Epstein-Barr Virus Lytic Replication Requires Transcription and the Formation of a Stable RNA-DNA Hybrid Molecule at OriLyt, Journal of Virology, Mar. 2011, 85(6): 2837-2850.
Rowe, M. et al., Epstein-Barr Virus (EBV)-associated Lymphoproliferative Disease in the SCID Mouse Model: Implications for the Pathogenesis of EBV-positive Lymphomas in Man, The Journal of Experimental Medicine, Jan. 1991, 173(1): 147-158.

(Continued)

*Primary Examiner* — Dennis Heyer
*Assistant Examiner* — Daniel M Podgorski
(74) *Attorney, Agent, or Firm* — Howson & Howson LLP; Mary E. Bak

(57) ABSTRACT

In an effort to discover therapies for treating diseases caused by EBV, a novel screening assay for identifying compounds that reactivate EBV latent infection and a family of small molecules based on a tetrahydrocarboline backbone were discovered. Specifically, the compounds have the structure of the formula (I), wherein $R^1$-$R^{11}$ are defined herein and activate/reactivate EBV in a variety of cell types in a patient and are, therefore, useful in preventing or treating EBV-positive cancer, optionally with an anti-viral agent. In screening these compounds, novel compositions, EBV-positive cell lines, and methods are provided. (Formula I)

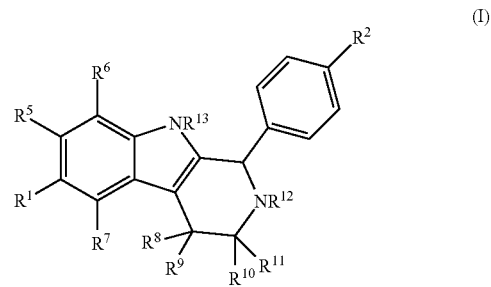

12 Claims, 17 Drawing Sheets

(56) References Cited

OTHER PUBLICATIONS

Shirley, C.M. et al., Bortezomib induction of C/EBPβ mediates Epstein-Barr virus lytic activation in Burkitt lymphoma, Blood, Jun. 2011, 117(23): 62907-6303.

International Search Report dated Dec. 10, 2014 in international stage (International Application No. PCT/US14/53415, filed Aug. 29, 2014).

Written Opinion dated Dec. 10, 2014 in international stage (International Application No. PCT/US14/53415, filed Aug. 29, 2014).

Auld, DS et al, Mar. 2008, Characterization of Chemical Libraries for Luciferase Inhibitory Activity, J. Med. Chem., 51(8):2372-2386.

Daigle, D, Jan. 2010, Upregulation of STAT3 Marks Burkitt Lymphoma Cells Refractory to Epstein-Barr Virus Lytic Cycle Induction by HDAC Inhibitors, J. Virol. 84(2):993-1004; on line publn Nov. 2009.

Daigle, D et al., Jun. 2011, Valproic Acid Antagonizes the Capacity of Other HDAC Inhibitors to Activate the Epstein-Barr Virus Lytic Cycle, J. Virol. 85(11):5628-5643; online publn Mar. 2011.

Daugen, A. et al., Sep. 2003, The Discovery of Tadalafil: A Novel and Highly Selective PDE5 Inhibitor. 1: 5,6,11,11a-Tetrahydro-1H-imidazo[1',5':1,6]pyrido[3,4-b]indole-1,3(2H)-dione Analogues, J. Med. Chem., 46(21):4525-4532.

Deng, Z., et al., Nov. 2001. Identification of acidic and aromatic residues in the Zta activation domain essential for Epstein-Barr virus reactivation. J. Virol. 75:10334-10347.

Fukayama, M and Ushiku, T. Sep. 2011, Epstein-Barr virus-associated gastric carcinoma., Pathology—Research and Practice, 207(9):529-537.

Gao, X., et al., Jul. 2001. 12-O-tetradecanoylphorbol-13-acetate induces Epstein-Barr virus reactivation via NF-κB and AP-1 as regulated by protein kinase C and mitogen-activated protein kinase. Virology 286:91-99.

Ghosh, SK et al, Jan. 2012, Histone deacetylase inhibitors are potent inducers of gene expression in latent EBV and sensitize lymphoma cells to nucleoside antiviral agents., Blood, 119:1008-1017; publ online Dec. 2011.

Gottschalk, S. et al, Feb. 2005, Post-Transplant Lymphoproliferative Disorders. Annu. Rev. Med. 56:29-44; online pub Aug. 2004.

Griner, EM and Kazanietz MG., Apr. 2007, Protein kinase C and other diacylglycerol effectors in cancer. Nature Rev., 7(4):281-294.

Gutierrez, MI et al., Apr. 1996, Switching viral latency to viral lysis: A novel therapeutic approach for Epstein-Barr virus-associated neoplasia., Cancer Res. 56(5):969-972.

Hamilton-Dutoit, SJ et al., Oct. 1993, Epstein-Barr virus latent gene expression and tumor cell phenotype in acquired immunodeficiency syndrome-related non-Hodgkin's lymphoma., Am. J. Pathol., 143(4):1072-1085.

Kenney, S. et al, May 1998, Gene Therapy Strategies for Treating Epstein-Barr Virus-Associated Lymphomas: Comparison of Two Different Epstein-Barr Virus-Based Vectors., Hum. Gene Ther. 9(8):1131-1141.

Klein, E. et al., Feb. 2007, Epstein-Barr virus infection in humans: from harmless to life endangering virus—lymphocyte interactions. Oncogene 26(9):1297-1305.

Loren, AW et al., Feb. 2003, Post-transplant lymphoproliferative disorder: a review. Bone Marrow Transplantation, 31(3):145-155.

Macmahon, EM et al, Oct. 1991, Epstein-Barr virus in AIDS-related primary central nervous system lymphoma. Lancet 338(8773):969-973.

Miller, G. et al., 2007, Lytic cycle switches of oncogenic human gammaherpesviruses. Adv. Cancer Res. 97:81-109.

Moore, SM et al, Jul. 2001, Induction of Epstein-Barr Virus Kinases to Sensitize Tumor Cells to Nucleoside Analogues. Antimicrob. Agents and Chemo. 45(70):2082-2091.

Nakagawa, Y. Jul. 2012, Artificial Analogs of Naturally Occurring Tumor Promoters as Biochemical Tools and Therapeutic Leads., Biosci., Biotechnol., and Biochem.,76:1262-1274.

Pasternak, A et al, Feb. 2012, Stimulation of Glucose-Dependent Insulin Secretion by a Potent, Selective sst3 Antagonist., ACS Med. Chem. Lett., 3(4):289-293.

Perrine, SP et al, Mar. 2007, A phase 1/2 trial of arginine butyrate and ganciclovir in patients with Epstein-Barr virus-associated lymphoid malignancies. Blood, 109:2571-2578, publ online Nov. 2006.

Raab-Traub, N., Dec. 2002, Epstein-Barr virus in the pathogenesis of NPC. Semin. Cancer Biol., 12(6):431-441.

Ragoczy, T and G. Miller, Jun. 2001, Autostimulation of the Epstein-Barr Virus BRLF1 Promoter Is Mediated through Consensus Sp1 and Sp3 Binding Sites., J. Virol. 75(11): 5240-5251.

Testa, B and J. Caldwell, May 1996, "Prodrugs Revisited: The "Ad Hoc" Approach as a Complement to Ligand Design", Medicinal Research Reviews, 16(3):233-241.

Thompson, S. et al., Oct. 2010, Development of a high-throughput screen for inhibitors of Epstein-Barr virus EBNA1. J. Biomol. Screening 15(9):1107-1115.

Thorley-Lawson, DA Aug. 2005, EBV the prototypical human tumor virus—just how bad is it? J. Allergy Clin. Immunol. 116(2):251-261.

Yates, JL et al, Feb. 1985, Stable replication of plasmids derived from Epstein-Barr virus in various mammalian cells. Nature 313(6005):812-815.

Young, LS, Rickinson, AB., Oct. 2004, Epstein-Barr virus: 40 years on. Nature Rev. Cancer 4(10):757-768.

Zhang, JH et al., 1999, A Simple Statistical Parameter for Use in Evaluation and Validation of High Throughput Screening Assays. J. Biomol. Screening 4(2):67-73.

\* cited by examiner

A.

A.

B.

C.

D.

E.

F.

A.

B.

C.

METHODS AND COMPOSITIONS FOR RE-ACTIVATING EPSTEIN-BARR VIRUS AND SCREENING COMPOUNDS THEREFOR

STATEMENT REGARDING FEDERALLY SPONSORED RESEARCH OR DEVELOPMENT

This invention was made with government support under grant No. R01 CA085678 awarded by the National Institutes of Health. The government has certain rights in this invention.

CROSS-REFERENCE TO RELATED APPLICATIONS

This application is a national stage of International Patent Application No. PCT/US2014/053415, filed Aug. 29, 2014, which claims the benefit of the priority of US Provisional Patent Application No. 61/872,673, filed Aug. 31, 2013 (expired), which priority applications are incorporated herein by reference.

BACKGROUND

Epstein-Barr Virus (EBV) is a human herpes virus that infects over 90% of the world's population (Rickinson, 2007, Epstein-Barr Virus., 5th ed., Wolters Kluwer Health/Lippincott Williams & Wilkins, Philadelphia and Kieff, 2007, Epstein-Barr Virus and its replication, 5th ed., Wolters Kluwer Health/Lippincott Williams & Wilkins, Philadelphia). Primary EBV infection is the major cause of infectious mononucleosis. However, EBV persists as a latent infection in, and drives formation of, many lymphoid and epithelial malignancies, including Burkitt's lymphoma (BL), Hodgkin lymphomas, nasopharyngeal carcinoma (NPC), and gastric carcinoma (GC) (Thorley-Lawson, 2005, J. Allergy Clin. Immunol. 116:251-261, quiz 262; Klein, 2007, Oncogene 26:1297-1305; Raab-Traub, 2002, 12:431-441; and Fukayama, 2011, Pathol., Res. and Prac., 207:529-537). Latent infection with EBV is a major cause of post-transplant lymphoproliferative disease in immuno-suppressed patients (Loren, 2003, Bone Marrow Transplantation, 31:145-155 and Gottschalk, 2004, Post-Transplant Lymphoproliferative Disorders, Annu. Rev. Med.) and greatly enhances risk of developing non-Hodgkin and primary CNS lymphomas in the HIV-positive population (Hamilton-Dutoit, 1993, Am. J. Pathol., 143:1072-1085 and MacMahon, 1991, Lancet 338:969-973). Most EBV associated cancers contain viral DNA that exists predominantly as a latent infection in which only a limited set of viral genes are expressed (Young, 2004, Nature Rev. Cancer 4:757-768). These latency associated genes are implicated in host-cell proliferation and survival, and latent EBV can directly promote tumor progression.

Current chemotherapeutic treatments of EBV-positive cancers include broad spectrum cytotoxic drugs that ignore the EBV-positive status of tumors. A recently proposed approach to treat EBV-positive cancers involves the induction of EBV lytic cycle followed by administration of antiviral drugs (Gutierrez, 1996, Cancer Res. 56:969-972; Kenney, 1998, Hum. Gene Ther. 9:1131-1141; and Moore, 2001, Antimicrob. Agents and Chemo. 45:2082-2091). This targeted "oncolytic therapy" requires the initiation of EBV lytic cycle and expression of viral kinases, which phosphorylate nucleoside analogues, e.g., gancyclovir (GSV), by converting the pro-drug to an active, selective suicide substrate for the viral and cellular DNA polymerases. This strategy aims to lower side effects associated with standard chemotherapy presently used to treat lymphomas and provides a molecular targeted therapeutic strategy by exploiting the biology of a key etiologic disease factor.

Several limitations of viral "oncolytic therapy" exist. For example, most existing methods activate/reactivate the lytic life-cycle in only a low percentage of latently infected cells. Many of the antiviral drugs are toxic; and most of the viral vectors are cell-type restricted or cell line specific. In addition, out of many known chemical activators of the EBV lytic cycle, only the histone deacetylase inhibitors derived from butyrate analogues have been tested in clinical trials (Perrine, 2007, Blood 109:2571-2578; and Ghosh, 2012, Blood, 119:1008-1017). In one clinical trial, arginine butyrate was found to be efficacious but was not tolerated due to toxicity, while sodium butyrate (NaB) was found to have unsuitable pharmacokinetics. More recent studies have screened clinically approved drugs for potential activators for latent EBV and identified bortezomib as an activator of latent EBV in a limited number of EBV positive BL cells (Shirley, 2011, Blood 117:6297-6303).

To date, no single EBV activator consistently reactivates EBV in all EBV positive cell lines (Miller, 2007, Adv. Cancer Res. 97:81-109 and Daigle, 2011, J. Virol. 85:5628-5643). Nor have any small molecules, including histone deacetylase (HDAC) inhibitors, proven safe or effective in clinical trials for treatment of EBV positive cancers.

What is needed in the art are small molecule compounds which active latent EBV and are effective in treating EBV positive cancers.

BRIEF DESCRIPTION OF THE DRAWINGS

FIG. 1A includes the data using episomal plasmids pHEBO-Hp-Luc or pHEBO-Zp-Luc to generate stable cell lines in EBV positive LCL281, Mutul, or Raji cells. Stable cell lines were then assayed for luciferase activity (luminescence) after treatment with DMSO (−) or 2 mM NaB (+). In FIG. 1B, the Mutul-Hp-Luc stable cell line (containing pHEBO-Hp-Luc in Mutul cells) was assayed for luciferase dependent luminescence at 0, 0.01, 0.1, 0.5, 1.0 or 2.0 mM NaB. In FIG. 1C, Mutul-Hp-Luc cells were assayed for optimal cell density in 384 well plates upon treatment with either 0.1% DMSO or 2 mM NaB for 48 h. Cells were plated at 0.01, 0.05, 0.1, 0.25, 0.5, or $1.0 \times 10^6$ cells per mL. Error bars represent standard deviation (SO) from the mean.

FIG. 2A is a scatter plot showing the analysis of Mutul-Hp-Luc cells in 384 well formats for statistical robustness. The plot is of the luciferase-dependent luminescence values for Mutul-Hp-Luc cells treated with DMSO (black dots under about 5000) or with 2 mM NaB (gray dots between 20000 and 30000) for 48 h. The Z-factor was determined to be 0.72. FIG. 2B is a scatter plot of luminescence values for HTS campaign of the ChemDiv library. The well number is indicated on the X-axis. FIG. 2C is a scatter plot of data from HTS of ChemDiv screen (FIG. 2B) re-sorted according to the fold induction of luminescence relative to DMSO. FIG. 2D is a flow chart of the screening campaign and validation studies. FIG. 2E is a bar graph for the confirmation luciferase assay for 9 positive hits delivered individually in each well at 10 μM. Positive controls include NaB, TPA, and doxorubicin (Doxo).

FIGS. 3A-3F are the dose response curves for compounds 1-5 titrated 2-fold starting from 10 μM concentration. The $EC_{50}$ and R-values are indicated in each panel.

FIG. 4A are Western blots of EA-0 and ZTA expression in EBV-positive cell lines treated with DMSO, NaB, TPA and compounds 1-5 for 72 h. 13-Actin is loading control. Cell lines include Mutul, Mutu-LCL281, Mutu-LCL352, B95.8-LCL 178, Mutu-LCL 178, Akata, and JSC1. FIGS. 4B-E are bar graphs illustrating real-time RT-PCR analysis of EA-0 (left panels) and ZTA expression (right panels) in EBV-positive cell lines, treated with DMSO, NaB, TPA or the indicated compounds for 48 h. Cell lines include Mutul (4B graphs), Mutu-LCL 178 (4C graphs), C666-1 (4D graphs), and Akata (4E graphs).

FIG. 5A is a FACS analysis of the percentage of GFP-positive (lytic) cells in Mutul-Hp-GFP cells after 72 h of treatment with 2% DMSO, 2 mM NaB, 20 ng/mL TPA or 1 μM of compound. FIG. 5B is a FACS scan of GFP-positive (lytic) Mutul-H-GFP cells after 72 h of treatment with DMSO (black), NaB or compound wherein the gate separates the GFP-positive population. FIG. 5C illustrates the percentage of VCA-positive (lytic) Mutul cells determined by FACS analysis after 96 h of treatment with DMSO, NaB or compound. FIG. 5D is a FACS analysis of the percentage of GFP-positive (lytic) cells in B95.8 LCL352 containing pHEBO-Hp-GFP cells after 72 h of treatment with 2% DMSO, 2 mM NaB, 20 ng/mL TPA or 1 μM of compound.

FIG. 6A is the scheme showing the order and timing of the assay. Mutul-Hp-Luc were seeded at 0.2 million per mL and treated with Compound 4. Compound 4 was added again 48 h. Freshly made GCV was added on Day 2 for 4 days twice a day, in the morning and 8 h later. Cell viability was measured either with Resazurin 5 days after the first Compound 4 treatment, or the cells were stained with Trypan blue on Day 6. FIG. 6B is a bar graph showing the percentage of live cells treated with compounds or controls with (gray bars) or without (black bars) GCV, for 6 days, as noted in FIG. 6A. Live cells were counted by the Trypan Blue stain exclusion method. FIGS. 6C-6F are bar graphs illustrating the resazurin cytotoxicity assay on cells treated with compounds and controls for 5 days, according to experimental scheme in FIG. 6A. Different concentrations of Compound 4 combined with GCV (gray bars) or without GCV (black bars) were used. Cell viability was measured as a percentage of DMSO-treated control cells. 590 nm fluorescence values are proportionate to the cell viability. Cells tested include EBV-positive Mutul (FIG. 6C), Akata (FIG. 6D), DG75 (FIG. 6E), and Mutu-LCL352 (FIG. 6F). Daily viability assay for Mutul cells treated with either DMSO, NaB, compound 4 (0.5 μM) with or without GCV was measured. FIG. 6G is a line graph plotting the daily measurements of the viability of Mutul cells treated with DMSO (●), NaB (■), 0.5 μM of compound 4 (▲), DMSO+GCV using resazurin, (✻) NaB+GCV (□) using resazurin, or 0.5 μM of compound 4+GCV using resazurin (✻) (FIG. 6G). FIGS. 6H-6J are bar graphs illustrating the resazurin cytotoxicity assays on EBV-negative cells DG75 (FIG. 6H), Akata- (FIG. 6I), or BJAB (FIG. 6J) treated identically as described for FIGS. 6C-6F.

FIG. 7A is Mutul cells treated with 2% DMSO, 2 mM NaB, 20 ng/mL TPA, or 1 μM compound for 48 h, immunoblotted, and probed for acetylation of histone H3 and β-actin. FIG. 7B is Mutu-LCL352 cells treated and probed as in described in FIG. 7A. FIG. 7C is Mutul cells treated with controls or compounds for 0.5 h, immunoblotted, and probed for phosphorylated forms of p90RSK, p53, p38MAPK, S6, total MAPK, and β-actin.

FIGS. 9A-9C are luciferase reporter assays with Rp-Luc (FIG. 9A), ZpLuc (FIG. 9B), or Hp-Luc (FIG. 9C) treated with either 1 μM DMSO or compound 4 with the addition of ZTA or RTA expression vector as indicated. Error bars represent SDM, and p-values for compound 4 response. FIG. 9D is a Western blot of Zta and β-actin from 293 transfected cells used for luciferase assays.

SUMMARY OF THE INVENTION

Figure 1:
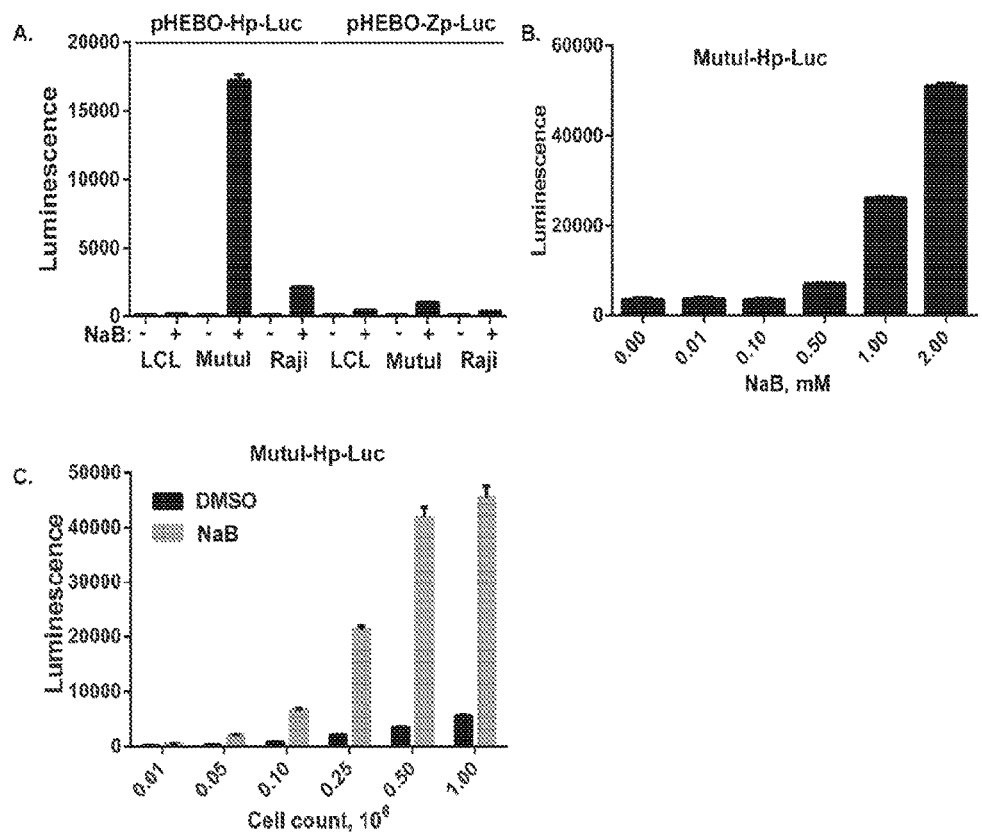
FIGS. 1A-1C are bar graphs illustrating the development of a high-throughput assay for EBV lytic reactivation.

In one aspect, a method for activating Epstein-Barr virus (EBV) is provided and includes administering a compound of formula (I), wherein $R^1$-$R^{13}$ are defined herein, or a pharmaceutically acceptable salt or prodrug thereof, to a subject in need thereof.

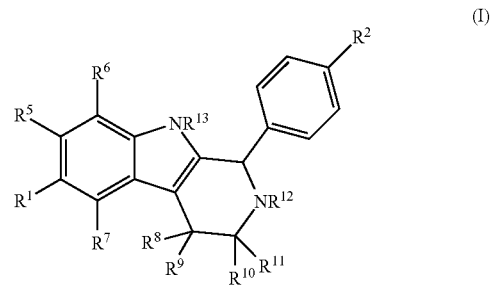

In another aspect, a method for preventing or treating EBV-positive cancer is provided and includes administering a compound of formula (I) noted herein to a subject in need thereof.

In a further aspect, a method of preventing post-transplant lymphoproliferative disease is provided and includes administering a compound of formula (I) described above to an immunosuppressed subject.

In yet another aspect, a kit is provided and includes (i) an anti-viral agent; and (ii) a compound of formula (I) described herein. In one embodiment, the anti-viral agent is gancyclovir.

In still a further aspect, a composition is provided and comprises an EBV-derived vector comprising a reporter gene that provides a measurable signal upon expression, wherein expression is under the operable control of an EBV lytic cycle promoter responsive to the EBV-encoded lytic cycle activator protein ZTA.

In another aspect, an EBV-positive cell line stably carrying a vector composition described herein is provided. In one embodiment, the cell is selected from among EBV positive cell lines LCL, Mutul, Raji, BL, LCL, PEL and NPC.

In a further aspect, a method for identifying small molecule activators of EBV lytic cycle gene expression is provided and includes contacting a cell line described herein with a test compound and measuring expression in the cell line of the reporter signal, wherein measurable expression of the reporter signal indicates that the test compound activates EBV lytic activity.

In yet another aspect, a method for treating or retarding growth of EBV-positive cancer in a mammalian subject is provided and includes treating a subject in need thereof with a test compound screened by a method described herein to induce lytic cycle of EBV-infected cells.

Other aspects and advantages of the invention will be readily apparent from the following detailed description of the invention.

DETAILED DESCRIPTION OF THE INVENTION

In recognizing the need in the art for therapies for treating diseases caused by EBV, the inventors identified a family of small molecules based on a tetrahydrocarboline backbone. These tetrahydrocarboline compounds unexpectedly activate/reactivate EBV in a variety of cell types in a patient. By doing so, these compounds target malignant cancer cells in which EBV is or has been intentionally or unintentionally activated. In one embodiment, the tetrahydrocarboline compounds discussed herein reactivate EBV lytic markers ZTA and EA-D in all EBV positive cell lines independent of the type of latency. In another embodiment, the compounds reactivate a higher percentage of latently infected cells than histone deacetylase (HDAC) inhibitors. In a further embodiment, the compounds reactivate a higher percentage of latently infected cells than phorbol esters. In still another embodiment, the compounds show low toxicity to EBV-negative cells.

Advantageously, the tetrahydrocarboline compounds are selective to EBV-positive cells and have low toxicity to EBV-negative cells. The term "low toxicity" as used herein refers to a $CC_{50}$ of 50 µM or less. These characteristics ensure that these compounds do not affect the healthy cells of the patient and permit more effective treatment. Further, the patient experiences considerable fewer side effects due to this selective cancer targeting regimen. This finding is integral in the treatment of certain cancers which are linked to EBV infection and where there are no known small molecule drug therapies.

The inventors found that these tetrahydrocarboline compounds are highly selective in killing EBV infected cells alone or in combination with an anti-viral agent. In one embodiment, the tetrahydrocarboline compounds additively or synergistically function with anti-viral agents for selective killing of EBV positive cells.

The terms "patient" and "subject" are used interchangeably and refer to a mammal, preferably a human, who was at one time infected with EBV and in whom the EBV infection is now latent. The patient may be an adult or child. A "patient" or "subject" may also include a veterinary or farm animal, a domestic animal or pet, and animals normally used for clinical research. In one embodiment, the patient or subject is a human.

By "EBV-positive" disease is meant certain neoplastic conditions or diseases caused by the presence of EBV infection or latent infection. The terms "neoplastic disease" and "cancer" are used interchangeably herein and refer to a disease or condition in which a patient has an abnormal mass of tissue due to an abnormal proliferation of cells. The abnormal proliferation of cells may result in a localized lump, be present in the lymphatic system, or may be systemic. In another embodiment, the neoplastic disease is caused by latent EBV infection. In one embodiment, the neoplastic disease is benign. In another embodiment, the neoplastic disease is pre-malignant, i.e., potentially malignant neoplastic disease. In a further embodiment, the neoplastic disease is malignant, i.e., cancer. EBV-positive neoplastic diseases (cancers) caused by EBV or EBV latent infection may be treated using the compounds, compositions and methods described herein. In one embodiment, the neoplastic disease is an epithelial cancer. In another embodiment, the neoplastic disease is a lymphoid cancer. In another embodiment, the neoplastic disease is Burkitt's lymphoma, non-Hodgkin lymphoma, or primary CNS lymphoma. In another embodiment the neoplastic disease is nasopharyngeal carcinoma. In another embodiment, the neoplastic disease is gastric carcinoma. Still another EBV-positive disease is post-transplant lymphoproliferative disease. Still other EBV-related neoplastic diseases are anticipated to respond to the methods and compositions described herein.

The tetrahydrocarboline compounds, therefore, are useful in the treatment or prevention of a variety of conditions/diseases. In one embodiment, the tetrahydrocarboline compounds are useful in methods for treating a disease caused by latent EBV infection. In another embodiment, the tetrahydrocarboline compounds are useful in methods for treating EBV-positive cancer. In a further embodiment, the tetrahydrocarboline compounds are useful in methods for preventing post-transplant lymphoproliferative disease.

I. The Compounds

As discussed above, the inventors found tetrahydrocarboline dione compounds which are useful for treating neoplastic disease caused by EBV. The term "tetrahydrocarboline compound" as used herein refers to compounds having the following backbone, wherein substituents may be optionally bound to one or more of the unsubstituted carbon atoms of the backbone:

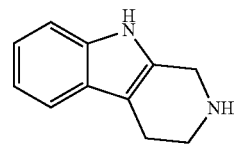 [SMILES: c1ccc2c3c([nH]c2c1)CNCC3]

In one embodiment, the compounds have following backbone, wherein substituents may be optionally bound to one or more of the unsubstituted carbon atoms of the backbone or the nitrogen atom of the amide functional group.

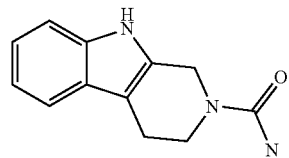 [SMILES: NC(=O)N1CCc2c([nH]c3ccccc23)C1]

In a further embodiment, the compounds discussed herein have the following structure of formula (I), or a pharmaceutically acceptable salt or prodrug thereof.

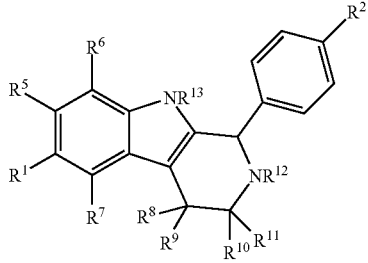
(I)

In this structure:

i. $R^1$ is H, $C_1$ to $C_6$ alkyl, $C_1$ to $C_6$ alkoxy, or halogen. In one embodiment, $R^1$ is $C_1$ to $C_6$ alkoxy or halogen. In another embodiment, $R^1$ is methoxy or chlorine.

ii. $R^2$ is H, $C_1$ to $C_6$ alkyl, or $C_1$ to $C_6$ alkoxy. In one embodiment, $R^2$ is $C_1$ to $C_6$ alkoxy or $C_1$ to $C_6$ alkoxy. In a further embodiment, $R^2$ is methyl or methoxy.

iii. $R^3$ is optionally substituted aryl or heteroaryl. In one aspect, $R^3$ is optionally substituted aryl. In one embodiment, $R^3$ is optionally substituted phenyl. In a further embodiment, $R^3$ is phenyl substituted with one or more of H, $C_1$ to $C_6$ alkyl, $C_1$ to $C_6$ alkoxy, or $C(O)(C_1$ to $C_6$ alkoxy). In yet another embodiment, $R^3$ is phenyl substituted with one $C_1$ to $C_6$ alkoxy, wherein said alkoxy is methoxy. In still a further embodiment, $R^3$ is 2-methoxy-phenyl.

iv. In another aspect, $R^3$ is optionally substituted heteroaryl. In one embodiment, $R^3$ is optionally substituted thiophene. In another embodiment, $R^3$ is thiophene substituted with one or more of H, $C_1$ to $C_6$ alkyl, $C_1$ to $C_6$ alkoxy, or $C(O)(C_1$ to $C_6$ alkoxy). In a further embodiment, $R^3$ is thiophene substituted with one $C(O)(C_1$ to $C_6$ alkoxy). In still another embodiment, $R^3$ is 2-$C(O)OCH_3$-thiophen-3-yl.

v. $R^4$ is H or optionally substituted $C_1$ to $C_6$ alkyl. In one embodiment, $R^4$ is H.

vi. $R^5$ to $R^{11}$ are, independently, selected from among H and $C_1$ to $C_6$ alkyl. In one embodiment, $R^5$ is H. In another embodiment, $R^6$ is H. In a further embodiment, $R^7$ is H. In yet another embodiment, $R^8$ is H. In still a further embodiment, $R^9$ is H. In another embodiment, $R^{10}$ is H. In a further embodiment, $R^{11}$ is H.

vii. $R^{12}$ is H, $C(O)OR^3$, $C(O)NR^3R^4$, or $SO_2R^3$.

viii. $R^{13}$ is H, optionally substituted aryl, or optionally substituted heteroaryl. In one embodiment, $R^{13}$ is H. In another embodiment, $R^{13}$ is optionally substituted aryl. In a further embodiment, $R^{13}$ is the following moiety, wherein $R^{14}$ is, independently, H, halogen, $C_1$ to $C_6$ alkyl, $C_1$ to $C_6$ alkoxy, or $C_1$ to $C_6$ trifluoroalkyl; n is 1 to 5; and said $R^{14}$ is located at any position on the benzene ring.

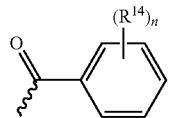
$(R^{14})_n$

In another aspect, the tetrahydrocarboline compound is of formula (II), (III), (IV), or (V), wherein $R^1$-$R^{11}$ and $R^{13}$ are defined above.

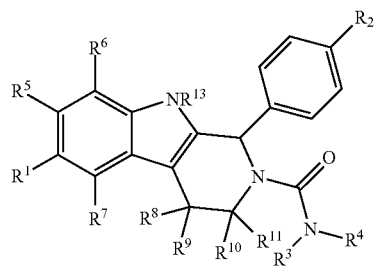
(II)

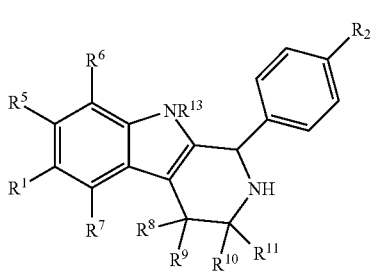
(III)

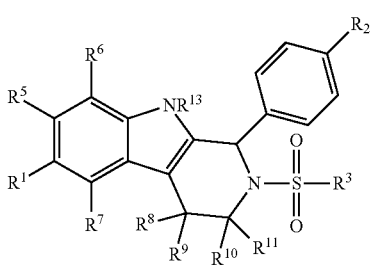
(IV)

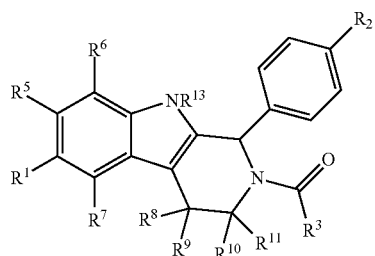
(V)

In a further aspect, the tetrahydrocarboline compound is one or more of the following compounds:

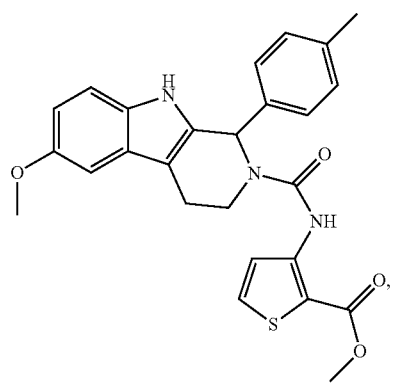

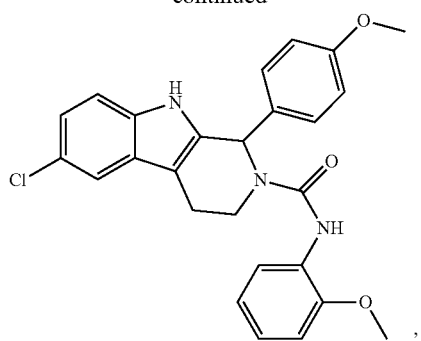
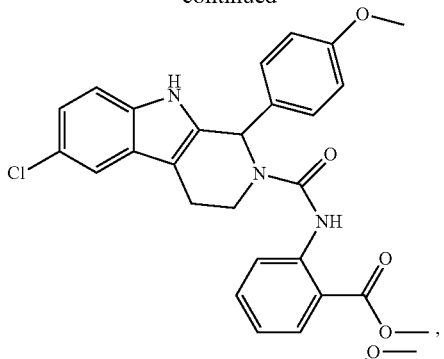
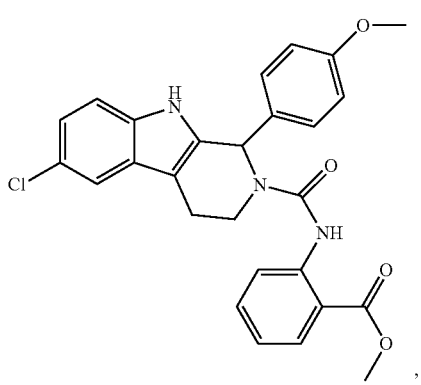
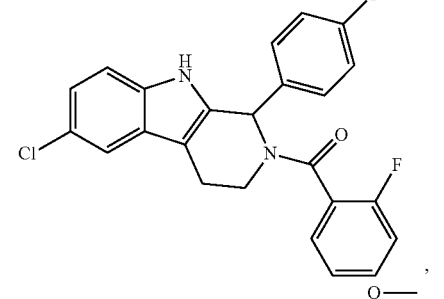
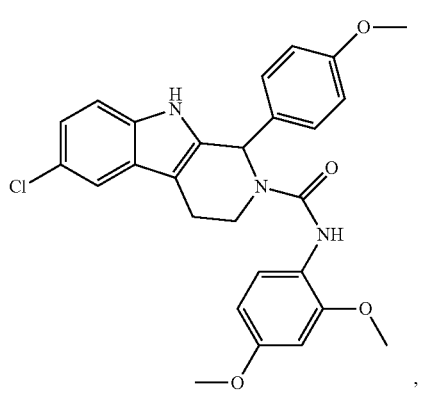
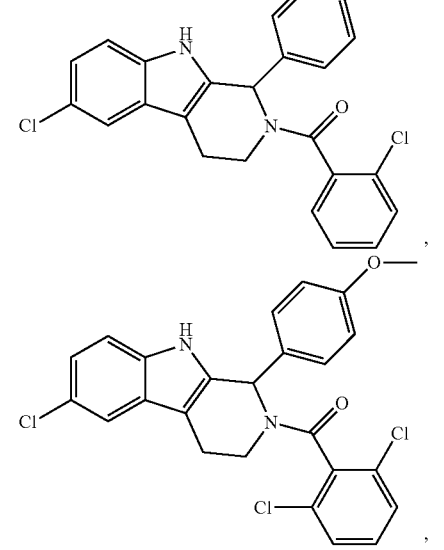

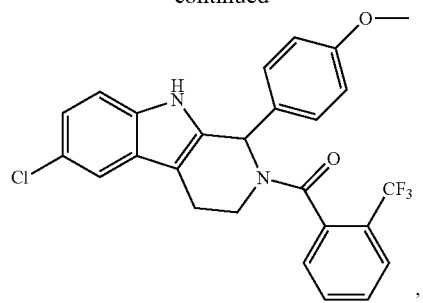
,
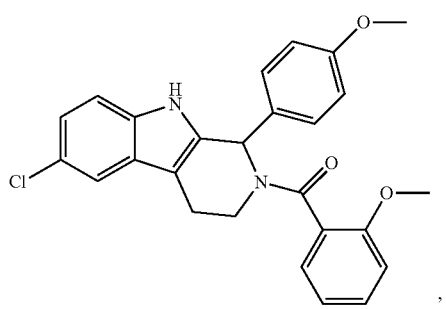
,
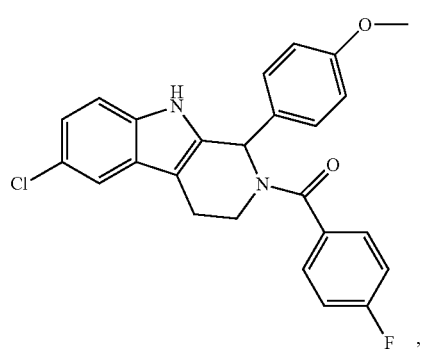
,
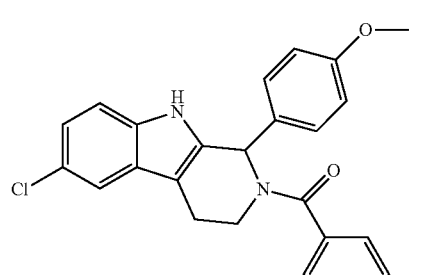
,
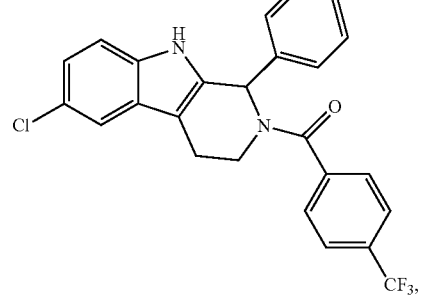
,
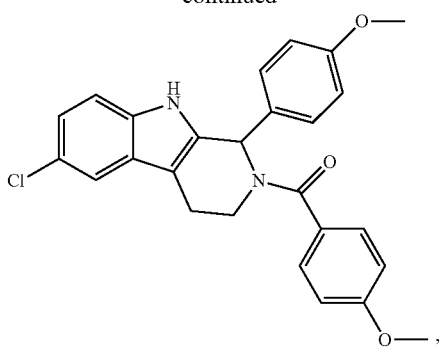
,
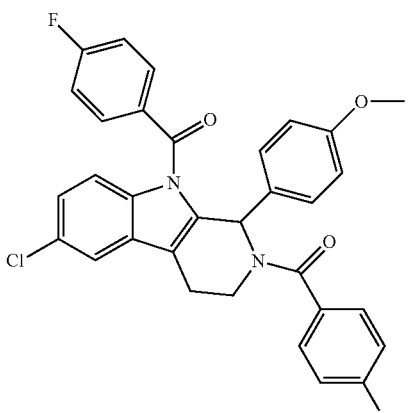
,
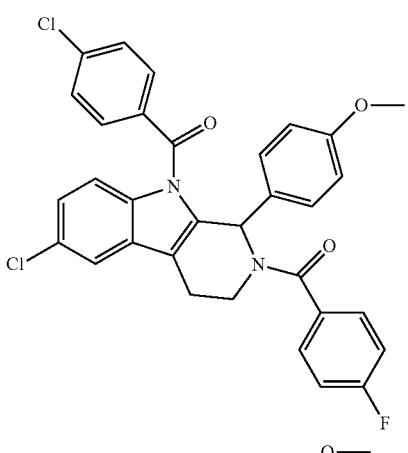
,
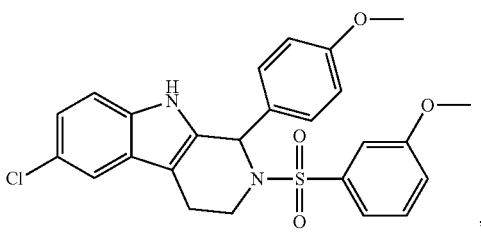
,
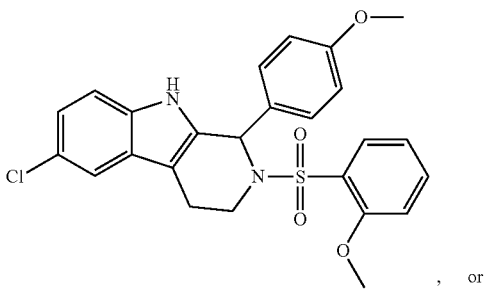
, or -continued

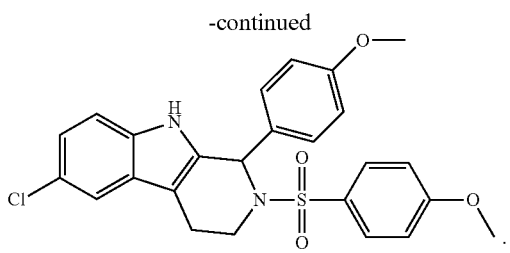

An "alkyl" group as used herein refers to saturated aliphatic hydrocarbon groups. An alkyl may have straight- or branched-chains. In one embodiment, an alkyl group has 1 to about 10 carbon atoms (i.e., $C_1$, $C_2$, $C_3$, $C_4$, $C_5$, $C_6$, $C_7$, $C_8$, $C_9$, or $C_{10}$), or ranges there between. In another embodiment, an alkyl group has 4 to about 10 carbon atoms (i.e., $C_4$, $C_5$, $C_6$, $C_7$, $C_8$, $C_9$, or $C_{10}$), or ranges there between. In a further embodiment, an alkyl group has 5 to about 10 carbon atoms (i.e., $C_5$, $C_6$, $C_7$, $C_8$, $C_9$, or $C_{10}$), or ranges there between.

The term "substituted alkyl" refers to an alkyl group having one or more substituents including, without limitation, hydrogen, halogen, CN, OH, $NO_2$, amino, aryl, heterocyclic, heteroaryl, alkoxy, and aryloxy.

"Alkoxy" refers to the group R—O— where R is an alkyl group, as defined above. Exemplary $C_1$-$C_6$ alkoxy groups include but are not limited to methoxy, ethoxy, n-propoxy, i-propoxy, n-butoxy and t-butoxy.

The term "substituted alkoxy" refers to an alkoxy group having one or more substituents on the alkyl chain including, without limitation, hydrogen, halogen, CN, OH, $NO_2$, amino, aryl, heterocyclic, heteroaryl, alkoxy, and aryloxy.

The term "halogen" as used herein refers to Cl, Br, F, or I groups.

The term "aryl" as used herein refers to an aromatic, carbocyclic system, e.g., of about 6, 7, 8, 9, 10, 11, 12, 13 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, carboxyalkyl (C(O)Oalkyl), trifluoroalkyl such as $CF_3$, aryloxy, alkoxy, aryl, or heteroaryl. Desirably, a substituted aryl group is substituted with 1, 2, 3, or 4 groups.

The term "heteroaryl" as used herein refers to a stable, aromatic 5, 6, 7, 8, 9, 10, 11, 12, 13 to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1, 2, 3, 4 or 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, carboxyalkyl(C(O) Oalkyl), trifluoroalkyl such as $CF_3$, aryloxy, alkoxy, aryl, or heteroaryl. A substituted heterocycle or heteroaryl group may have 1, 2, 3, or 4 substituents.

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In one embodiment, pharmaceutically acceptable salts can be formed from organic and inorganic acids. Examples of useful organic and inorganic acids include, without limitation, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In another embodiment, pharmaceutically acceptable salts may also be formed from organic and inorganic bases. Examples of useful inorganic bases include, without limitation, alkali metal salts such as, e.g., sodium, lithium, or potassium, such as alkali metal hydroxides. Pharmaceutically acceptable salts may also be formed from organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmonoethanolammonium, diethanolamine, ethylenediamine, and the like. In one example, the base is selected from among sodium hydroxide, lithium hydroxide, potassium hydroxide, and mixtures thereof.

These salts, as well as other compounds, can be in the form of esters, carbamates, i.e., "pro-drugs", which convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons, 1996, which is herein incorporated by reference.

The compounds discussed herein also encompass "metabolites" which form by in vivo processing of the compounds.

II. Methods of Treatment of Diseases Mediated by Latent EBV Infection

In still another aspect, a method for treating a mammalian subject for an EBV-positive disease or cancer is provided. This method is based upon the fact that cells in which the EBV is latent cannot be successfully targeted by therapeutics. However, the inventors determined that if the virus is activated in latently-infected cells, the cells would then be vulnerable to therapeutic compounds, such as anti-viral or anti-cancer drugs or regimens. Therefore, in one aspect, a method for treating a mammalian subject for an EBV-positive disease comprises administering to a subject having an EBV-positive disease or EBV-positive cancer an effective amount of a composition, compound or formulation that induces or reactivates the lytic cycle of EBV-infected cells. In one embodiment, such compositions include one of the family of tetrahydrocarboline compounds described specifically herein. In another embodiment, such compositions include a compound screened and identified as a reactivator of EBV latent infection by the assay described below.

In still another embodiment, the method of treatment involves administering, following reactivation of the EBV lytic infection in the subject, an inhibitor of viral lytic replication or other pharmaceutical reagent that can target and retard growth of subject's cells demonstrating newly active EBV infection.

The components and steps of these treatment methods are described in detail below.

A. Pharmaceutical Formulations and Methods of Administration

As used herein and throughout this specification below for ease of review, the phrase "compounds of the invention" or "tetrahydrocarboline compounds" are used to refer to the specific compounds described herein as well as other latent EBV-activating compounds or molecules identified through use of the screening assay described in detail below.

The compounds of the invention may be formulated neat or with one or more excipient for administration. One of skill in the art would readily be able to determine suitable excipients based on the selected tetrahydrocarboline compound, patient, administration route, disease/condition being treated, among others. Not only may the composition be solid or liquid, but excipient(s) may be solid and/or liquid carriers. The carriers may be in dry or liquid form and must be pharmaceutically acceptable. The compositions are typically sterile solutions or suspensions.

Suitably, the tetrahydrocarboline compounds may be formulated for delivery to a patient by any suitable route including, e.g., transdermal, mucosal (intranasal, buccal, vaginal), oral, parenteral, intravenous, intratumoral, intranodal, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the tetrahydrocarboline compounds may be combined with one or more excipients. Examples of excipients which may be combined with the tetrahydrocarboline compound include, without limitation, solid carriers, liquid carriers, adjuvant, antioxidants, suspending agent, syrup, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, thickening agents, or viscosity regulators. See, the excipients in "Handbook of Pharmaceutical Excipients", 5$^{th}$ Edition, Eds.: Rowe, Sheskey, and Owen, APhA Publications (Washington, D.C.), 2005 and U.S. Pat. No. 7,078,053, which are incorporated herein by reference. The selection of the particular excipient is dependent on the nature of the tetrahydrocarboline compound selected and the particular form of administration desired.

When the route of administration is oral, the composition may be any suitable conventional form, including, without limitation, the form of a capsule, caplet, gel tab, dispersible powder, granule, suspension, liquid, thin film, chewable tablet, rapid dissolve tablet, medical lollipop, or fast melt. In one embodiment, the composition is a liquid. In a further embodiment, the composition is a solid. In another embodiment, the composition is a suspension. One of skill in the art would readily be able to formulate the compositions discussed herein in any one of these forms.

Solid carriers include, without limitation, starch, lactose, dicalcium phosphate, microcrystalline cellulose, sucrose and kaolin.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

Liquid carriers may be utilized in preparing solutions, suspensions, emulsions, syrups and elixirs. In one embodiment, the tetrahydrocarboline compound is dissolved in a liquid carrier. In another embodiment, the tetrahydrocarboline compound is suspended in a liquid carrier. In one embodiment, the liquid carrier includes, without limitation, water, e.g., sterile water, organic solvents (such as glycerol, propylene glycol, liquid polyethylene glycol, dimethylsulfoxide (DMSO)), oils (such as fractionated coconut oil, arachis oil, corn oil, peanut oil, and sesame oil and oily esters such as ethyl oleate and isopropyl myristate), fats, cellulose derivatives such as sodium carboxymethyl cellulose, and non-ionic surfactants.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the tetrahydrocarboline compound may be combined with a suspending agent, including about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5 to about 5% of suspending agent.

In another embodiment, the tetrahydrocarboline compound may be combined with a syrup containing, e.g., about 10, 15, 20, 25, 30, 35, 40, 45, to about 50% of sugar.

In a further embodiment, the tetrahydrocarboline compound may be combined with an elixir containing, e.g., about 20, 25, 30, 35, 40, 45 to about 50% ethanol, and the like.

In another embodiment, the composition may be utilized as an inhalant or aerosol. When administered as an inhalant, the composition may be in fluid unit doses using the tetrahydrocarboline compound and a vehicle for delivery by an atomizing spray pump or by dry powder for insufflation. When administered as an aerosol, the composition may be in a pressurized aerosol container together with a gaseous or liquefied propellant, e.g., dichlorodifluoromethane, carbon dioxide, nitrogen, propane, and the like. Also optionally provided is the delivery of a metered dose in one or more actuations. When the composition is administered intranasally, the administration may be performed using a mist or spray.

The tetrahydrocarboline compounds may also be administered parenterally or intraperitoneally as solutions, suspensions, dispersions, or the like. Such pharmaceutical preparations may contain, e.g., about 25, 30, 35, 40, 45, 50, 55, 60, 65, 70, 75, 80, 85, to about 90% of the tetrahydrocarboline compound in combination with the carrier.

The tetrahydrocarboline compounds may also be administered via a vaginal ring or transdermal patch.

The effective dosage or amount of the tetrahydrocarboline compounds may vary depending on the particular tetrahydrocarboline compound employed, the mode of administration and the severity of the condition being treated. In one embodiment, the effective amount is about 0.01 mg/kg to 10 mg/kg body weight. In another embodiment, the effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 μg/kg, about 75 μg/kg, about 50 μg/kg, about 25 μg/kg, about 10 μg/kg, or about 1 μg/kg. However, the effective amount of the tetrahydrocarboline compound can be determined by the attending physician and depends on the condition treated, the compound administered, the route of delivery, the age, weight, severity of the patient's symptoms and response pattern of the patient.

The effective amount of the tetrahydrocarboline compound may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses. The number and frequency of dosages corresponding to a completed course of therapy will be determined according to the judgment of a health-care practitioner. The effective amounts described herein refer to total amounts administered for a given time period; that is, if more than one tetrahydrocarboline compound or a pharmaceutically acceptable salt thereof is administered, the effective amounts correspond to the total amount administered.

These dosage regimens may be adjusted to provide the optimal therapeutic response. For example, several divided doses of each component may be administered daily or the dose may be proportionally increased or reduced as indicated by the exigencies of the therapeutic situation. In one embodiment, the compounds or compositions discussed herein may be administered on a daily, monthly, or yearly basis. In one embodiment, daily administration is once. In another embodiment, daily administration includes divided units which are administered over the course of each day.

B. Administration with Additional Pharmaceutical Reagents

One or more of the tetrahydrocarboline compounds discussed herein may be administered in combination with other pharmaceutical agents, as well as in combination with each other. The term "pharmaceutical" agent as used herein refers to a chemical compound which results in a pharmacological effect in a patient.

One or more tetrahydrocarboline compounds described herein may be administered to a patient in need thereof with one or more of these pharmaceutical agents. In one embodiment, the tetrahydrocarboline compound is combined with one or more of these pharmaceutical agents, i.e., delivered to the patient concurrently. In another embodiment, the tetrahydrocarboline compound is delivered to the patient concurrently therewith one or more of these pharmaceutical agents. In a further embodiment, the tetrahydrocarboline compound is delivered prior to one or more of these pharmaceutical agents. In still another embodiment, the tetrahydrocarboline compound is delivered subsequent to one or more of these pharmaceutical agents. In one embodiment, the tetrahydrocarboline compound is administered with a chemotherapeutic. One of skill in the art would readily be able to select a chemotherapeutic for administration with one or more of the tetrahydrocarboline compounds based on the cancer being treated, patient physical condition, among others factors. In one embodiment, the chemotherapeutic is selected from among cisplatin, 5-fluorouracil, cyclophosphamide, oncovin, vincristine, prednisone, or rituximab.

One or more of the tetrahydrocarboline compounds may also be administered with an anti-viral agent. In one embodiment, the anti-viral agent is gancyclovir, acyclovir, valganciclovir, vidarabine, brivudine, cytarabine, idoxuridine, penciclovir, famciclovir. In another embodiment, the anti-viral agent is gancyclovir.

Histone deacetylase inhibitors may further be administered with one or more of the tetrahydrocarboline compounds discussed herein. One skilled in the art would be able to select a suitable histone deacetylase inhibitor. In one embodiment, the histone deactylase inhibitor is arginine butyrate, sodium butyrate, suerboylanilide hydroxamic acid (SAHA), or valproic acid.

The tetrahydrocarboline compounds may further be administered with one or more of a DNA methylation inhibitor. In one embodiment, the DNA methylation inhibitor is 5'-azacytidine.

The tetrahydrocarboline compound may further be administered with one or more proteasome inhibitor. One skilled in the art would be able to select a suitable proteasome inhibitor for use in the present invention. In one embodiment, the proteasome inhibitor is bortezamib.

The tetrahydrocarboline compound may further be administered concurrently, subsequent, or prior to additional reagents which are utilized for immunotherapy and/or in vaccines. Desirably, the immunotherapy and/or vaccines are tailored to the patient and specific disease/conditions being treated. In one embodiment, the immunotherapy and/or vaccines are tailored to the patient and specific cancer being treated. In another embodiment, an anti-viral agent is administered prior to, concurrently with, or subsequent to the compound. In a further embodiment, a chemotherapeutic is administered prior to, concurrently with, or subsequent to the compound.

C. Additional Treatment Protocols

The tetrahydrocarboline compounds described herein may be utilized to activate EBV. Chemotherapy and/or radiation therapy, in other embodiments, bolster the effects of the therapy described herein. Finally, immune-based therapies can eradicate residual disease and activate endogenous immune responses. Such combination approaches (surgery plus chemotherapy/radiation plus immunotherapy) are anticipated to be successful in the treatment of many cancers along with the methods described herein.

Still other adjunctive therapies for use with the methods and compositions described herein include, in one embodiment, acupuncture. In a further embodiment, the non-chemical treatment protocol is surgery. In yet another embodiment, the non-chemical treatment protocol is chiropractic care. In still another embodiment, the non-chemical treatment protocol is passive or active immunotherapy. In a further embodiment, the non-chemical treatment protocol includes X-rays. In still another embodiment, the non-chemical treatment protocol includes ultrasounds, among others. Still other method steps that can be included with or adjunctive to the methods described herein are diagnostic assessments, e.g., blood testing, to determine or monitor the progress of the infection, the course or status of the disease, relapse or any need for booster administrations of the compositions.

These additional treatment protocols may be administered prior to, concurrently with, or subsequent to administration of the tetrahydrocarboline compound. In one embodiment, radiation is administered prior to, concurrently with, or subsequent to the compound.

Doses of the tetrahydrocarboline compounds within the ranges described above may be used when the tetrahydrocarboline compound is administered in combination with an additional pharmacologically active reagent or in an additional treatment protocol. In another embodiment, lower doses of the tetrahydrocarboline compounds are useful when administered in combination with an additional pharmacologically active reagent. In still other embodiments, combination of the tetrahydrocarboline compound with another pharmacological agent or treatment protocol permits lower than usual dosages of the additional pharmacological agent or adjustment of the additional protocol regimen and/or lower doses of the tetrahydrocarboline compounds to achieve the desired therapeutic effect.

III. Kits Containing the Tetrahydrocarboline Compounds

Also provided are kits or packages of pharmaceutical formulations containing (i) the tetrahydrocarboline compound discussed above and used herein; and (ii) an anti-viral agent. In one embodiment, the tetrahydrocarboline compound is a compound of formula (I). Suitably, the kits contain one or more tetrahydrocarboline compounds as described herein and one or more anti-viral agent. Advantageously, for use in the kits, the tetrahydrocarboline compound and anti-viral agent are formulated for the desired delivery vehicle and route. In one embodiment, the kit is also includes a chemotherapeutic agent described above. For example, the tetrahydrocarboline compound and anti-viral agent can be formulated for oral delivery, parenteral delivery, vaginal ring, transdermal delivery, or mucosal delivery as discussed in detail above.

In one embodiment, the kit is designed for delivery at home. The kit may, therefore, include tubes or other containers, applicators, needles, syringes, and other appropriate packaging and instructions for use.

IV. Novel Assays and Assay Components for Identifying Compositions or Compounds that Induce EBV Lytic Cycle To enable identification of new chemical entities or compositions that induce the EBV lytic cycle, the inventors developed a novel and robust high throughput cell-based screening assay. Due to the need for improved efficacious therapeutics with lower toxicity and a decreased potential for recurrence of EBV-positive lymphoid malignancies, this cell-based method and its components were developed for the high throughput screening of thousands of compounds, e.g., 66,840 small molecule compounds.

In one aspect, a composition or component useful in the assay is an EBV-derived vector comprising a reporter gene that provides a measurable and/or detectable signal upon expression.

The backbone of the vector may be derived from any suitable bacterial plasmid backbone of which many are known. The vector is referred to as EBV-derived due to the EBV sequences present in it.

In the plasmid vector backbone, control elements are necessary when operably linked to the reporter gene to permit its transcription, translation and/or expression in a cell transfected with the plasmid vector. As used herein, "operably linked" sequences or sequences "in operable association" include both expression control sequences that are contiguous with the reporter gene of interest and expression control sequences that act in trans or at a distance to control the reporter gene of interest. This vector specifically employs an EBV lytic cycle promoter responsive to the EBV-encoded lytic cycle activator protein ZTA which is placed in operative association with the reporter gene to control its expression. In one embodiment, the EBV lytic cycle promoter responsive to the EBV-encoded lytic cycle activator protein ZTA useful in this vector is the promoter of the BZLF1 (Zp) immediate early gene encoding the ZTA lytic activator. In another embodiment the promoter is the promoter of the early lytic gene BHLF1 (Hp) responsive to ZTA transcription activation.

Other expression control sequences include appropriate transcription initiation, termination, enhancer sequences; efficient RNA processing signals such as splicing and polyadenylation (polyA) signals; sequences that enhance translation efficiency (i.e., Kozak consensus sequence); sequences that enhance protein stability; and when desired, sequences that enhance secretion of the encoded product.

In another embodiment, the vector further comprises a sequence encoding the EBV viral latent origin of replication oriP element. The oriP is a fragment of EBV DNA that assists the vector to replicate as a plasmid in EBV infected cells. In another embodiment the vector also contains a sequence encoding the EBV nuclear antigen 1 protein (EBNA1). EBNA1 activates the initiation of viral DNA replication through binding to specific sites in the oriP. In another embodiment, the vector also contains the hph gene from E. coli. In still a further embodiment, the vector comprises an antibiotic resistance gene. Such genes are commonly employed in plasmid construction and can include genes mediating resistance to antibiotics such as hygromycin B,β-lactams, amino glycosides, chloramphenicol, and trimethoprim.

Suitable "reporter gene" sequences as used in the vector include reporter genes that encode a fluorescent protein that generates a fluorescent signal or reporter genes that encode an enzyme, that when exposed to a suitable substrate produces an enzymatic signal, or colorimetric signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), or luciferase. Still other suitable reporter genes include those encoding membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

Figure 8:
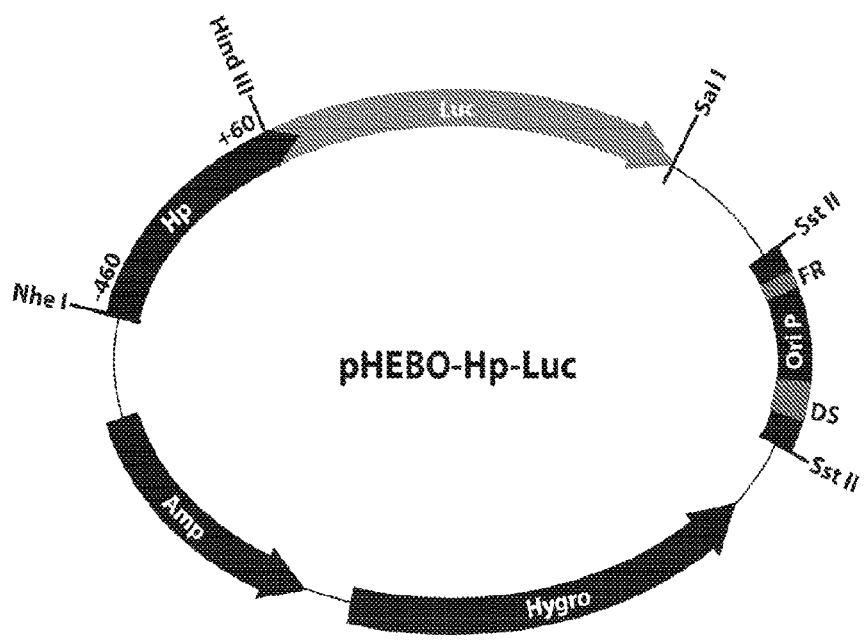
FIG. 8 is a schematic map of plasmid pHEBO-Hp-Luc used in the examples which contains in a pBR322 backbone, the EBV BHLF1 promoter Hp cloned upstream of the luciferase gene, and an oriP of EBV flanked by the EBV DS and FR region sequences, with the coding sequences for the hph gene from *Escherichia coli* and antibiotic resistance genes for hygromycin B and ampicillin.

An exemplary embodiment of a useful backbone vector to create the vector of this invention is the EBV oriP-containing, hygromycin resistant vector pHEBO (Yates, 1985, Nature 313:812-815; Sugden et al, 1985, Mol. Cell. Biol., 5(2):410-414). To create reporter constructs that can be maintained as a chromatinized episome similar to latent EBV genome, the inventors cloned EBV promoter Hp or EBV promoter Zp upstream of the luciferase reporter gene into the pBR322-backbone plasmid pHEBO to generate pHEBO-Hp-Luc (FIG. 8) and pHEBO-Zp-Luc. The constructions of these vectors are described in the examples below. However, one of skill in the art, given this teaching, may select other vector backbones, and other replaceable elements, e.g., reporter gene and antibiotic resistance genes that will operate similarly to pHEBO-Hp-Luc and pHEBO-Zp-Luc.

In addition to the vectors described above, another component of the assays designed to screen and identify activators of the EBV lytic cycle include EBV-positive cell lines that are transfected with, and stably carry the above-described vectors. Such cell lines may be selected from known and available EBV positive cell lines, such as LCL, Mutul, Raji, BL, LCL, PEL and NPC. These cells lines are commercially or publically available via sources such as the American Type Culture Collection and other universities and research sources. The stable cell lines are generated by transfection with the vector constructs described in this specification for a suitable time, followed by selection of the transfected cells with suitable amounts of the antibiotic corresponding to the selected antibiotic resistance gene in the vector. In the examples, below, the antibiotic resistance gene was hygromycin. After a suitable period of incubation to permit only the cells containing plasmids with the antibiotic resistance gene to grow, stable antibiotic-resistant, vector-containing cells were obtained and used in the assays. One of skill in the art may select from among known transfection protocols, including temperatures and times of incubation and amounts and concentrations of reagents to generate the cell lines, according to the teachings of this specification.

Thus, the novel assay described herein utilizes an EBV positive cell line (e.g., the BL cell line Mutul) carrying a stable episome-based vector comprising a reporter construct (e.g., pHEBO-Hp-Luc or pHEBO-Hp-GFP) that responds with high-sensitivity and dynamic range to the EBV-encoded lytic cycle activator protein ZTA.

Thus, in one embodiment an assay method for identifying small molecule activators of EBV lytic cycle gene expression comprises employing an EBV positive cell line that stably carries an EBV-derived vector comprising a reporter gene that provides a measurable signal upon expression. The expression of the reporter gene is under the operable control of an EBV lytic cycle promoter responsive to the EBV-encoded lytic cycle activator protein ZTA. This cell line is contacted with a test compound. After a suitable contact period, the cell line is examined for the signal generated by the expression of the reporter gene. Measurable or detectable expression of the reporter signal indicates that the test compound activates EBV lytic activity.

In one embodiment of this assay, the contact between the test compound and the stable cell line, e.g., incubation of the stable cell culture with the test compound, occurs for including and between 12 hours through and including 96 hours. In one embodiment, the contact is about 12 hours. In one embodiment, the contact is about 24 hours. In another embodiment the contact is about 36 hours. In another embodiment the contact is about 48 hours. In another embodiment the contact is about 60 hours. In another embodiment the contact is about 72 hours. In another embodiment the contact is about 84 hours. In another embodiment the contact is about 96 hours. Still other embodiments involve any number or fraction of hours between the 12 to 96 hour range. Depending upon the strength of the test compound, it is anticipated that lower contacting times may also be useful in this assay.

In another aspect, the contacting step further comprises incubating the cells under suitable conditions comprising incubation at 37° C. or exposing the cells to 5% $CO_2$. These conditions can be selected by one of skill in the art depending upon the selection of the cell and the reporter. Still another step involved in the contacting involves adding a reporter protein substrate to the culture when the reporter is an enzymatic gene and requires a substrate to produce its detectable, measureable signal.

In still another embodiment, the cell culture of the stable cell line to which the test compound is added can be present in a single plates or a multi-well plate for high-throughput assay steps. In one embodiment, a suitable cell density for the contacting step is between and including $2 \times 10^5$ cells per mL to $1 \times 10^6$ cells per mL. In one embodiment, the cell density is $2 \times 10^5$ cells per mL. In another embodiment, the cell density is $3 \times 10^5$ cells per mL. In another embodiment, the cell density is $3 \times 10^5$ cells per mL. In another embodiment, the cell density is $4 \times 10^5$ cells per mL. In another embodiment, the cell density is $5 \times 10^5$ cells per ml. In another embodiment, the cell density is $6 \times 10^5$ cells per mL. In another embodiment, the cell density is $7 \times 10^5$ cells per mL. In another embodiment, the cell density is $8 \times 10^5$ cells per mL. In another embodiment, the cell density is $9 \times 10^5$ cells per mL. In another embodiment, the cell density is $1 \times 10^6$ cells per mL. Still other embodiments involve any number or fractional density of cells per mL of hours between the $2 \times 10^5$ cells per mL to $1 \times 10^6$ cells per mL density range. In an example of the assay described below the cells are present in a 384 multi-well plate, with a cell density of 25,000 cells/well.

The contacting step also involves a suitable concentration of the test compound per mL or per well. In one embodiment, the cells are contacted with between and including 0.1 nM and including $1 \times 10^5$ nM (or 10 µM) concentration of test compound. In one embodiment the test compound concentration is 0.1 nM. In another embodiment, the test compound is at least 0.2, 0.3, 0.4, 0.5, 0.6, 0.7, 0.8, 0.9, 1, 2, 3, 4, 5, 6, 7, 8, 9, 10 nM. In another embodiment, the test compound is at least $1 \times 10^2$ nM. In another embodiment, the test compound is at least $1 \times 10^3$ nM. In another embodiment, the test compound is at least $1 \times 10^4$ nM. In another embodiment, the test compound is at least $1 \times 10^5$ nM. Still other embodiments involve any number or fractional concentration of test compound between the concentration values identified above.

In one embodiment, the measuring of the effect compound can be visually detected by a color change or fluorescence. For reporter genes requiring a substrate for signal generation, the method further employs introducing a suitable substrate to the cell line/test compound combination. In yet another embodiment, the method involves comparing the magnitude of the reporter signal in response to the test compound in the cell line to the magnitude of the reporter signal caused by a positive or negative control. In one embodiment, the positive control is sodium butyrate. In another embodiment, the negative control is DMSO.

The measuring step itself depends upon the type of reporter gene employed in the vector. For example, the measuring step can involve performing fluorescence activated flow cytometry, where the reporter is GFP or RFP. In another embodiment, the measuring step can involve detecting luminescence, e.g., where the reporter is luciferase. Still other measurement methods include immunostaining the contacted cells for the presence of EBV viral capsid antigen on the cell surface.

Yet a further aspect of the assay method can involve performing a counterscreen to determine the ability of the test compound to inhibit purified reporter activity in vitro in a different cell line. An exemplary counterscreen is described in Example 2 below.

The assay thus enables a determination and identification of molecules that robustly activate EBV lytic cycle gene expression. In one embodiment, the measuring step involves determining the number or percentage of contacted cells in which lytic activation was induced compared to cells contacted with a positive control. Induction of lytic activation in an equal or greater percentage of cells compared to control-contacted cells is an indication of a test compound activator. In another embodiment, the measuring step comprises measuring at least one of a reporter signal to background ratio, a signal to noise ratio, and cell toxicity.

In one embodiment, measurement of a signal to background ratio of 10:1 or greater permits identification of a test compound as an EBV lytic activator.

In another embodiment, measuring a signal to noise ratio of 5:1 or greater permits identification of a test compound as an EBV lytic activator. In still another embodiment, the method involves identifying test compounds that create a signal greater than 15-20 fold above a negative control can identify a test compound as an EBV lytic activator. In still another method, the degree of cell toxicity can also establish a useful vs. not useful EBV lytic activator. In still another embodiment, a suitable EBV lytic activator has an $EC_{50}$ activity between 150 and 170 nM, as described in Example 2 below.

As described in the examples and embodiments below, this assay was used to screen a total of 66,840 compounds. A number of structurally related molecules that robustly activate EBV lytic cycle gene expression in multiple cell types, including BLs, LCLs, and NPC derived cell lines, were found. These newly identified reactivators are identified as Compounds 1 to 4 described herein and in the Examples below.

In yet a further embodiment, kits for performance of this assay are contemplated that contain the vector constructs, substrates, and all components necessary to practice the assay.

V. Embodiments Described Herein

In one embodiment, a method for activating EBV is provided and includes administering a compound of formula (I), or a pharmaceutically acceptable salt or prodrug thereof, to a subject in need thereof, wherein $R^1$ is H, $C_1$ to $C_6$ alkyl, $C_1$ to $C_6$ alkoxy, or halogen; $R^2$ is H, $C_1$ to $C_6$ alkyl, or $C_1$ to $C_6$ alkoxy; $R^3$ is optionally substituted aryl or heteroaryl; $R^4$ is H or optionally substituted $C_1$ to $C_6$ alkyl; and $R^5$ to $R^{11}$ are, independently, selected from among H and $C_1$ to $C_6$ alkyl. In one aspect, the EBV infection is latent in malignant tumor cells. In another aspect, the compound has low toxicity to EBV-negative cells. In a further aspect, the compound is selective for EBV-positive cells.

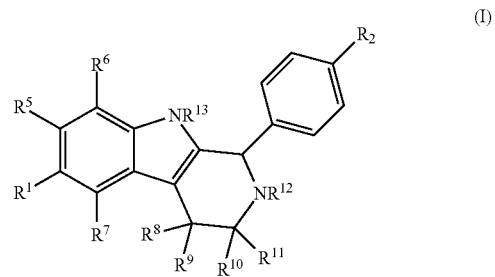

In another embodiment, a method for preventing or treating EBV-positive cancer is provided and includes administering a compound of formula (I) described above to a subject in need thereof. In one aspect, the method further includes administering an anti-viral agent such as gancyclovir.

In a further embodiment, a method of preventing post-transplant lymphoproliferative disease is provided and includes administering a compound of formula (I) as described above to an immunosuppressed subject.

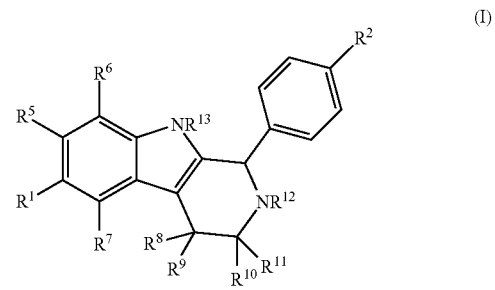

In yet another embodiment, any of the methods described herein may be performed using a compound selected from among the following.

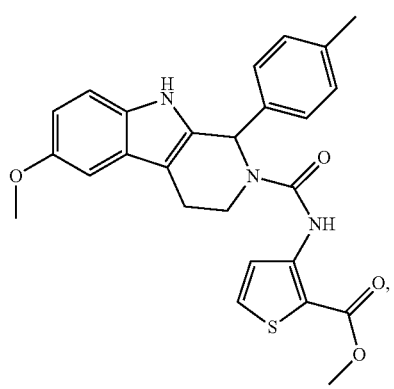
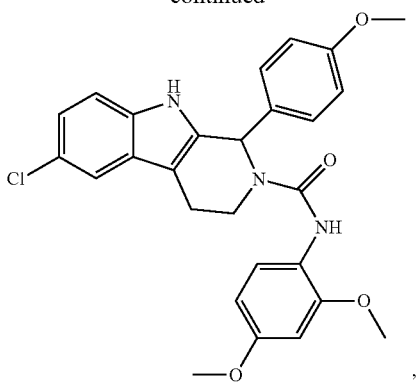
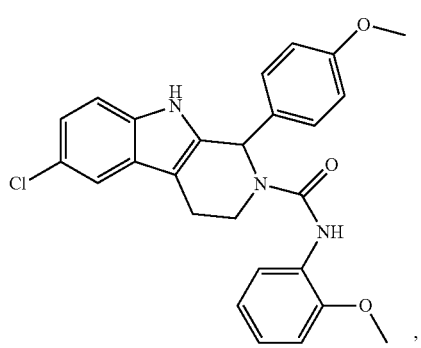
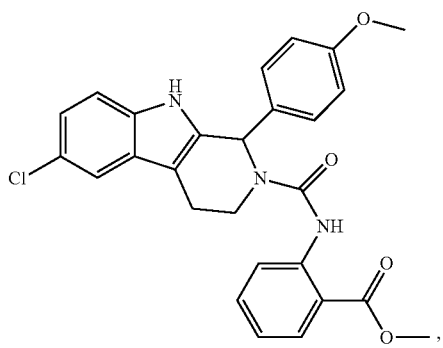
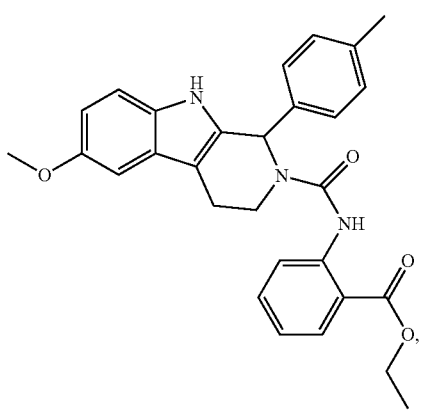
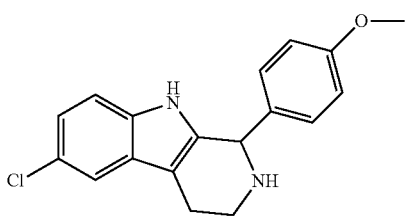
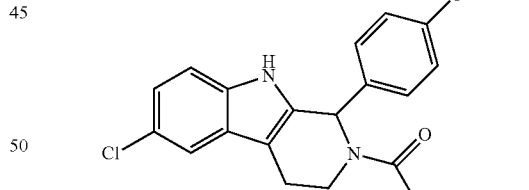
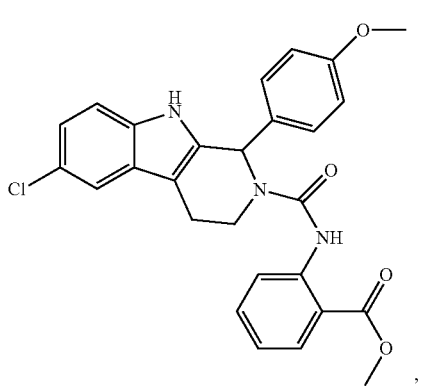
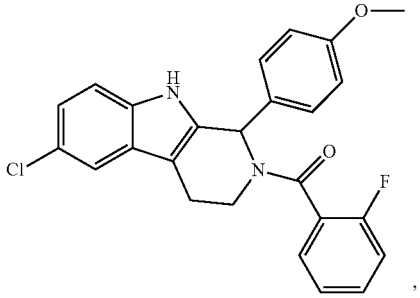

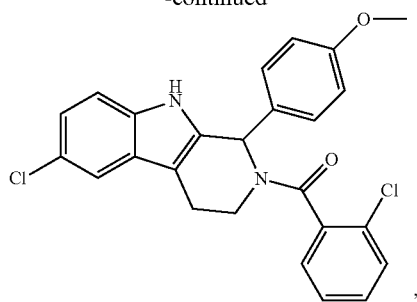
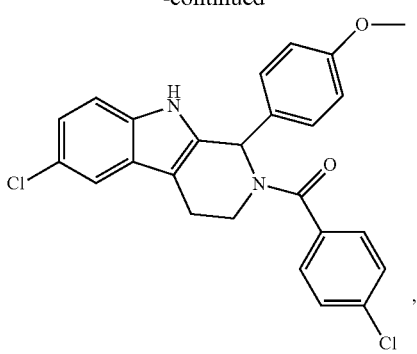
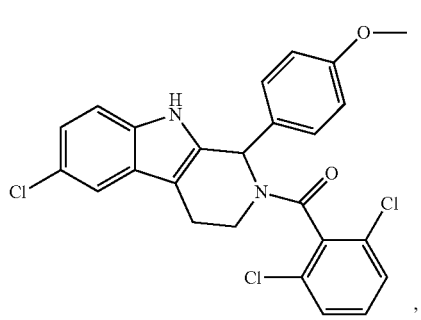
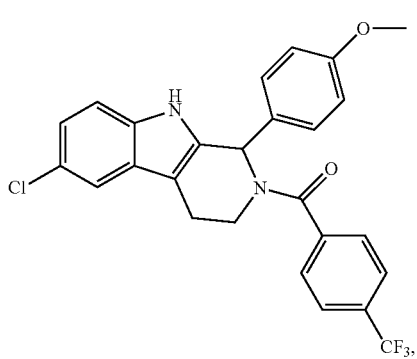
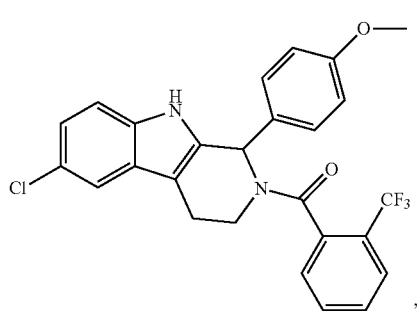
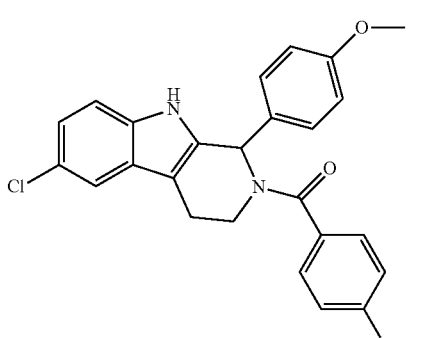
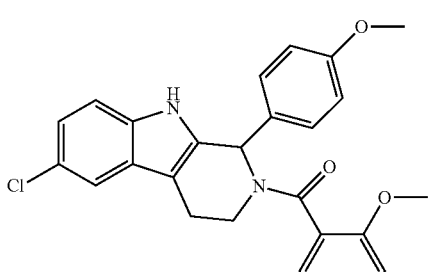
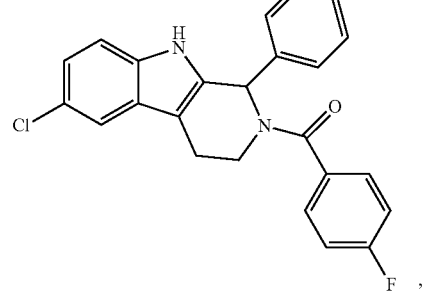
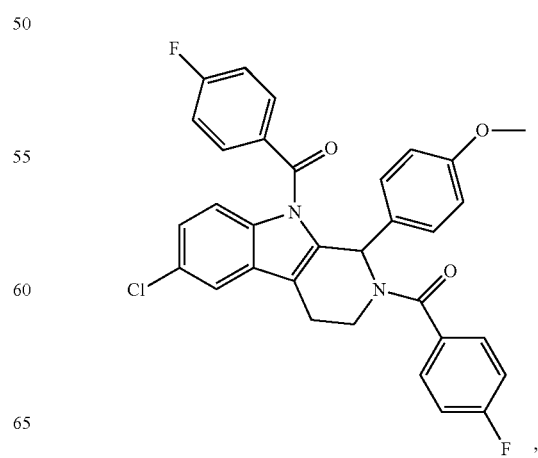

-continued

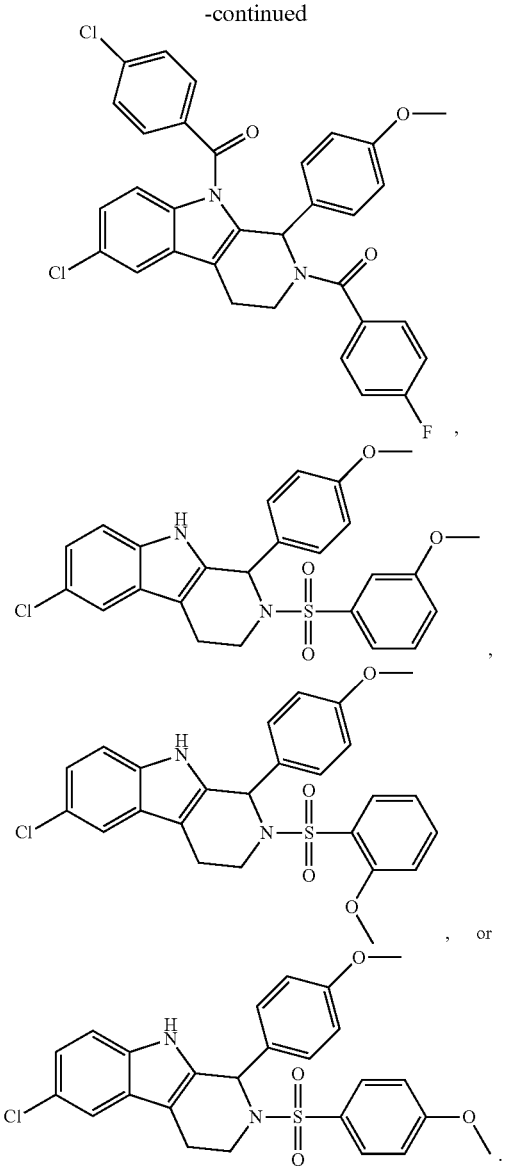

, or

In still a further embodiment, a kit is provided and contains (i) an anti-viral agent; and (ii) a compound of formula (I) as described above. In one aspect, the kit further includes a chemotherapeutic. In another aspect, the kit further contains an anti-viral agent such as gancyclovir.

In another embodiment, a composition is provided and contains an EBV-derived vector comprising a reporter gene that provides a measurable signal upon expression, wherein expression is under the operable control of an EBV lytic cycle promoter responsive to the EBV-encoded lytic cycle activator protein ZTA.

In yet a further embodiment, an EBV-positive cell line stably carrying a composition containing an EBV-derived vector comprising a reporter gene that provides a measurable signal upon expression, wherein expression is under the operable control of an EBV lytic cycle promoter responsive to the EBV-encoded lytic cycle activator protein ZTA, is provided. In one aspect, the cell is selected from the group consisting of EBV positive cell lines LCL, Mutul, Raji, BL, LCL, PEL and NPC.

In a further embodiment, a method for identifying small molecule activators of EBV lytic cycle gene expression is provided and includes contacting a cell line fas described herein with a test compound; and measuring expression in the cell line of the reporter signal, wherein measurable expression of the reporter signal indicates that said test compound activates EBV lytic activity.

In yet another embodiment, a method for treating or retarding growth of EBV-positive cancer in a mammalian subject is provided and includes treating a subject in need thereof with a test compound screened by the method described in the preceding paragraph to induce lytic cycle of EBV-infected cells.

VI. Examples

The following examples are illustrative only and are not intended to limit the present invention.

EXAMPLE 1

Assay Development and Methods Used

To develop a high-throughput, cell-based assay for identification of small molecule activators of EBV lytic cycle gene expression, stable cell lines containing reporter genes under the control of EBV lytic cycle promoters for BZLF1 (Zp) or BHLF1 (Hp) were generated. BZLF1 is the immediate early gene encoding the ZTA lytic activator. BHLF1 is an early lytic gene highly responsive to ZTA transcriptional activation. To create reporter constructs that can be maintained as chromatinized episomes similar to latent EBV genome, the OriP-containing, hygromycin resistant vector pHEBO (Yates, 1985, Nature 313:812-815) was utilized. EBV promoters Hp and Zp were cloned upstream of the luciferase reporter gene in pHEBO to generate pHEBO-Hp-Luc and pHEBO-Zp-Luc. These plasmids were then used to generate stable episomal reporters in EBV positive cell lines LCLs, Mutul, and Raji.

A. Cell Culture

Akata (EBV+ BL), BJAB, Akata EBV-negative (EBV− BL), JSC-1 (EBV+/KSHV+PEL), DG75 (EBV+ BL), Mutul (EBV+ BL), C666-1 (EBV+ NPC), and 293 T cells were obtained from ATCC. LCL cell lines were made by in vitro immortalization with EBV by infecting B-lymphocytes isolated from blood obtained from different EBV-negative donors with either B95-8 or Mutu EBV strains. LCLs derived from Mutul were referred to as Mutu-LCLs. All cell lines had low passage and were cultured for no more than 1 month in RPM I supplemented with 13% heat inactivated FBS, 50 μg/mL Penicillin, and 1% Glutamax™ reagent (Invitrogen) at 37° C. and 10% $CO_2$. Cell concentration was maintained at 0.2-0.8 million per mL, and cell viability was over 90% for each cell line at the time of compound screening or before each treatment. For the assay development, confirmation assays, and dose-response curves, $10^4$ cells were plated in 96 well white plates. Drug treatments of were carried out in RPMI media supplemented with 5% FBS.

B. Immunoblotting

Cells were incubated with DMSO, 2 mM sodium butyrate (NaB), 20 μg/mL 12-O-tetradecanoyl phorbol-13-acetate (TPA) or 1 μM of compounds for 72 h, washed in PBS once and lysed in 1×Laemmii buffer. Protein extract equivalent to $10^5$ cells were loaded on 8-16% SDS-PAGE gels (Invitrogen) and transferred to nitrocellulose membranes (Millipore). Lytic reactivation was detected with a rabbit polyclonal anti-ZTA and mouse monoclonal anti-EA-D (Abcam) antibodies diluted in 5% evaporated milk and incubated with the membranes for 2 h at RT, or overnight at 4° C., followed by secondary anti-mouse or rabbit HRP-conjugated (Roche).

Rabbit antibodies against phospho-p38 MAPK, -S6, -p90RSK and -p53 West Pico were mixed into a PathScan® cocktail (Cell Signaling). West Femto (Thermo) and EC1 Prime (GE) were used to detect the proteins with Fujifilm® 1AS-3000 camera and software.

C. FACS Analysis and Immunofluorescence

For the immunofluorescence staining of viral capsid antigen, cells were fixed with 4% paraformaldehyde in PBS, washed and blocked with PBS containing 1% BSA. Anti-VCA antibody (Millipore) was used at 1:100 followed by antimouse R-phycoerythrin (PE)-conjugated antibody (Sigma). FACS analysis was used to analyze the percentage of PE-positive cells. LSR-II instrument and FACSDiva™ software (BD Biosciences) were used to analyze the samples. FlowJo® software was used to create graphs (Tree Star, Inc).

D. Real-Time PCR Analysis

Cells were incubated with DMSO, 2 mM NaB, 20 µg/mL phorbol ester (TPA) or 1 µM of compounds for 48 h. Total RNA was isolated with TRIzol® reagent and reverse-transcribed with random hexamers and SuperScript® II RT polymerase (maker). Primers used for amplification of EBV and cellular gene were described in Tempera, 2010, PLoS pathogens 6, c1001048

E. Luciferase and GFP Reporter Construction

BHLF1 promoter (Hp) or the BZ1F1 promoter (Zp) was cloned into pHEBO plasmid into NheI and HindIII restriction sites of pHEBO-luc plasmid (Yates, 1985, Nature, 313:812-815; and Deng, 2001, J. Virol. 75:10334-10347). To create pHEBO-GFP, most of luciferase gene was excised by BsrGI and HindIII sites and replaced with EGFP excised from pEGFP-N1 (Clontech). Mutul cells were transfected with the new pHEBO-Zp-luc, pHEBO-Hp-luc (FIG. 8) or pHEBO-Hp-GFP constructs and transfected cells were selected with 400 µg/mL of Hygromycin. After 2 weeks of selection, stable hygromycin-resistant cells were seeded at 5000 per well in 384 well white plates and assayed as described below.

For the Rp, Hp, and Zp stimulation assays, pHEBO-Hp-473-Luc was utilized, while Zp and Rp were inserted into pGL3-Basic plasmids (Promega). ZTA was cloned in pcDNA3 (Invitrogen), and RTA was expressed from pRTS1S-RTA (Ragoczy, 2001, J. Virol. 75, 5240-5251). All 293T cells were co-transfected with Renilla Luciferase control plasmid expressed from pGL4.74-[hRluc/TK] vector (Promega).

F. High-Throughput Screening Library

The Wistar Molecular Screening Facility small molecule library is a collection of both synthetic and natural products from commercial sources that can be grouped into three categories: (i) known bioactive compounds, including drugs; (ii) focused libraries aimed at specific target classes, e.g., kinases, ion channels, GPCRs; and (iii) diversity sets representing areas of chemical space. This library is comprised of Spectrum 2000, the NIH clinical collection, a 14,400 compound library from Maybridge, and a 50,000 compound library from ChemDiv. The Maybridge "Hit Finder" library represents lead-like diversity from the larger Maybridge screening collection (56,000). The ChemDiv library consists of a 30,000 compound "Discovery Chemistry" set of diverse lead-like small molecules, and 20,000 compounds from a "Target Specific" set, with subsets of compounds designed to target various enzymes and receptors. The Maybridge and ChemDiv libraries were formatted in self-deconvoluting mixtures (5XY) for high-throughput screening where each compound is represented twice in the screen, and mixed with 4 unrelated compounds in separate wells. This approach enables screens to be done 2.5-fold more efficient with respect to reagent and consumable consumption without sacrificing biological replicates or ability to rapidly identify bioactive compounds (Thompson, 2010, J. Biomol. Screening 15:1107-1115).

G. Results

To test the responsiveness of the Hp- and Zp-luciferase reporters to EBV lytic cycle activation in each cell type, luciferase expression in cells treated with or without sodium butyrate (NaB) was assayed. It was found that pHEBO-Hp-Luc in Mutul cells provided the most robust response (>20 fold) to NaB relative to other reporters and cell lines (FIG. 1A). The pHEBO-Hp-Luc Mutul stable cell line (referred to as Mutul-Hp-Luc) was therefore selected for further development of a high-throughput assay. For these experiments, NaB was used as a positive control compound for lytic activation and DMSO as a negative control. Also assessed was the assay's tolerance to DMSO and optimized response to NaB concentration, treatment time, and cell density. It was found that the assay tolerated as much as 2% DMSO.

A range of NaB concentrations was then tested to determine the maximum induction of luciferase and dose-dependency of the response. Treating Mutul-Hp-Luc cells with up to 2 mM NaB consistently produced high luciferase signals and a signal-to-background of 20-40-fold, with relatively low cell toxicity (FIG. 1B). Maximum luciferase stimulation achieved by 2 mM NaB after 48 h of treatment, with longer periods of exposure to 2 mM NaB led to a loss of cell viability. 48 h treatment was, therefore, chose for compound screening. It was also determined that 25,000 cells per well for a 384-well plate was sufficient to achieve maximum signal with 2 mM NaB (FIG. 1C).

To quantitatively assess the accumulative effect of these optimizations on assay's precision and accuracy to control conditions and validation for high throughput screening, the cellular response to DMSO and NaB in replicate 384-well assay plates prepared on 3 different days was also tested. For these experiments, one-half of each assay plate (n=192) was treated with DMSO and the other half with 2 mM NaB. The assay consistently yielded a Z-factor >0.7, a signal to noise (S/N) ratio >70, and a signal to background (S/B) ratio >7 (Zhang, 1999, J. Biomol. Screening 4:67-73) (FIG. 2A). Based on these data, the assay was sufficiently robust for high-throughput screening.

EXAMPLE 2

High-throughput Screening Process

Assay plates were prepared by seeding 25,000 Mutu-Hp-Luc cells in 50 µL of RPMI supplemented with 15% FBS in white opaque 384 well tissue culture plates (Corning), using a Biotek Microflo and a 5 µL cassette. Fifty nanoliters of test compound or DMSO was transferred to assay plates using a Janus MDT® NanoHead system (Perkin Elmer). Columns 1, 2, 23, and 24 received DMSO (0.2% final concentration). The remaining 320 wells in columns 3-22 received test compounds at a final concentration of 10 µM cumulative concentration/2 µM individual compound concentration/0.2% final DMSO concentration. Cells were incubated with compounds for 48 h at 37° C./5% $CO_2$. Twenty microliters of Steady-Glo® Luciferase Reagent (Promega) was added to assay plates and incubated for 15 minutes at room temperature. Plates were centrifuged and luminescence was measured on an EnVision® Excite multilabel microplate reader, using the ultrasensitive luminescence measurement technology (Perkin Elmer).

A. Compound Confirmation, Counterscreens and Quantitative Assessment of Compound Activity To confirm the activity of candidate compounds identified after deconvolution that exceeded the cutoff parameter, liquid stock from the screening library was retested as single compounds at a final concentration of 10 µM, using assay conditions identical to the primary high-throughput screen.

To eliminate confirmed actives that may interfere with the assay technology by inhibiting luciferase, the activity of the compounds were tested in a biochemical luciferase assay counterscreen (Auld, 2008, J. Med. Chem., 51:2372-2386). To quantitatively assess the activity and prioritize compounds for further follow-up, fresh liquid stocks prepared from powders were reformatted as a 10 point dilution series spanning at least 3-logs, starting at 10 µM, the initial screening concentration. Data for test compounds was normalized to DMSO and NaB (1 mM) plate controls to calculate fold stimulation and z-factor (σ is variance/standard deviations), µ is mean of positive (p) and negative (n) controls). Z-factor is a statistical measurement that assesses the quality of the assay and predicts if the assay can be useful in a high-throughput screening. Z factors above 0.5 are considered acceptable. The screen's Z-factor was above 0.

$$\text{fold stimulation} = \frac{\text{test\_well}}{\text{Avg\_DMSO}}$$

$$z \text{ factor} = 1 - \frac{3(\sigma_p - \sigma_n)}{|\mu_p - \mu_n|}$$

The average fold stimulation and three times the standard deviation of all compounds screened were calculated. The sum of these two aggregate values was used as an initial cutoff to identify active compound wells, i.e., any compound well that exhibited stimulation of luciferase greater than the cutoff was considered to contain an active molecule and used for subsequent deconvolution of the screening mixtures.

The relative $EC_{50}$ for each compound, i.e., the concentration of compound that produced 50% of the maximum effect, was calculated using a 4 point non-linear regression analysis (GraphPad Prism® 6 software). Error bars represent SD for each concentration of a compound. To assist with decision making points, compound activities were stratified into 4 categories:

1) actives—well defined top and bottom asymptotes, i.e., the bioactive compound cleanly maps to a unique well in both the horizontal and vertical dimensions;

2) ambiguous—incomplete stimulation, no top asymptote-100% induction, i.e., the bioactive compound maps to 2 or more wells in either dimension;

3) orphan—compounds with activity at a single concentration or steep Hill slopes, i.e., an orthogonal match could not be identified in the second dimension; or 4) inactive, i.e., fold-stimulation<cutoff parameter. Z factor was used to measure the statistical robustness of the high-throughput screening (Zhang, 1999, J. Biomolecular Screening, 4:67-73).

Compounds with activities that fall into class 1 and 2 were prioritized for further analysis.

B. Cell Viability Assays

Assay plates were prepared by seeding 25,000 Mutul cells in 50 µL of RPMI supplemented with 15% FBS in 384 well tissue culture plates (Nunc). One hundred nanoliters of test compounds or DMSO was transferred to assay plates using a Janus DMT® nanohead system (Perkin Elmer). Cells were incubated for 5 days at 37° C./5% $CO_2$ and viability was monitored by the addition of 20 µL of 500 µM resazurin (Sigma) and incubation for 4 h at 37° C. Plates were centrifuged and fluorescence intensity was measured at 590 nm on an Envision® Xcite multilabel microplate reader (Perkin Elmer).

Each compound was tested in triplicate at a single concentration of 10 µM in Mutul-Hp-Luc cells. The activity of 24 compounds that induced luciferase expression greater than two fold was confirmed in this assay.

C. Results

The average Z-factor and signal window for DMSO and 2 mM NaB treated wells of control plates throughout the screen was 0.698 and 9.17, respectively. The mean luciferase activity of all test wells in the screen was equal to the average luciferase activity of DMSO treated control wells on each assay plate. Using an initial cutoff of greater than 3 standard deviations from the mean DMSO control signal, 89 candidate activators of the EBV lytic life cycle were identified through this screen (FIGS. 2B and 2C). To confirm the activity of these candidate hits, a secondary confirmation assay was performed with compounds picked from the library source plates.

To eliminate the possibility that these compounds acted directly on the luciferase enzyme, and not on EBV, they were tested for their ability to inhibit purified luciferase in vitro. Many small molecules have been shown to inhibit the luciferase enzyme in vitro and stimulate luciferase activity in cell-based screens due to luciferase protein stabilization (Thorne, 2012, Chem. & Biol. 19:1060-1072). Fifteen of these 24 compounds with confirmed activity in the cell-based reporter gene assay inhibited recombinant luciferase, and thus were eliminated from further consideration. This screen/counterscreen scheme yielded 9 candidate activators of the EBV lytic life cycle for an overall hit rate of 0.013% (summarized in FIG. 1D).

To further investigate the activity of these compounds and the potential mechanism of action, fresh powder supplies of each compound were purchased, their mass and purity confirmed by LC/MS, and their activity retested in the cell-based reporter gene assay. Five out of these nine compounds confirmed activity comparable to 2 mM NaB (FIG. 2E). None of the 5 confirmed candidates showed significant inhibition of recombinant luciferase in vitro.

Remarkably, all five EBV activators shared similar structure belonging to the same chemical family.

Additional compounds were discovered and had confirmed activity in the cell-based reporter gene assay described above. See Table A.

| Compound # | Compound Structure |
|---|---|
| 10 | 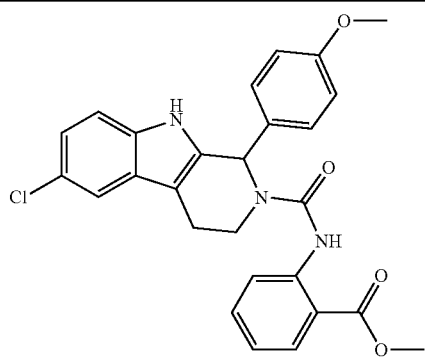 |

| Compound # | Compound Structure |
|---|---|
| 11 | 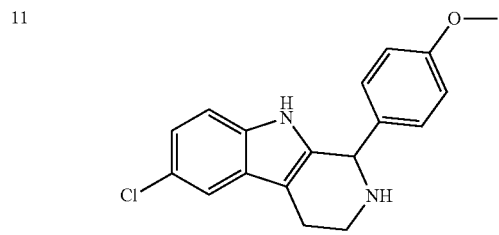 |
| 12 | 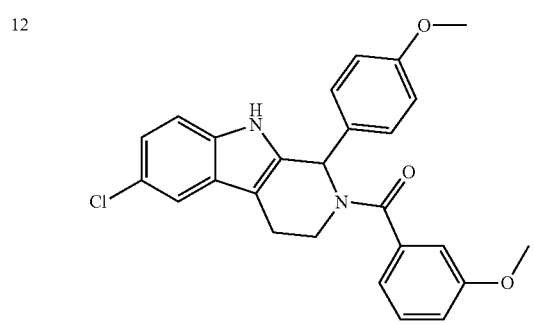 |
| 13 | 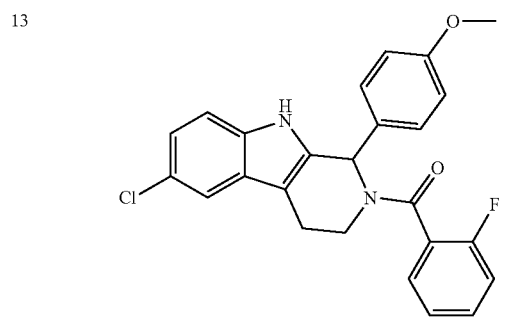 |
| 14 | 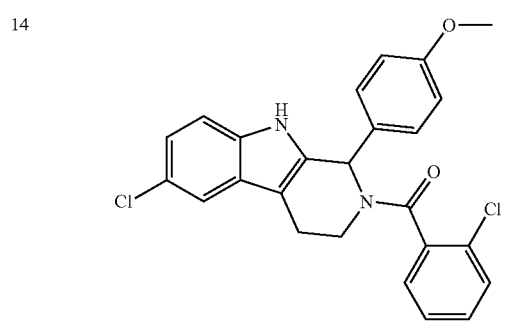 |
| 15 | 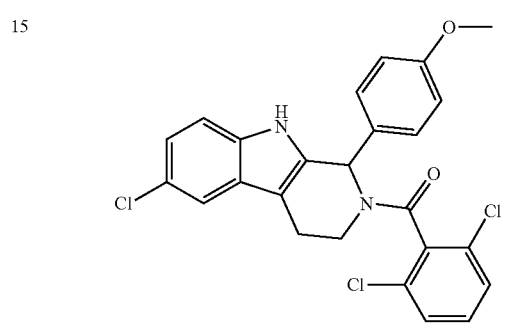 |
| Compound # | Compound Structure |
|---|---|
| 16 | 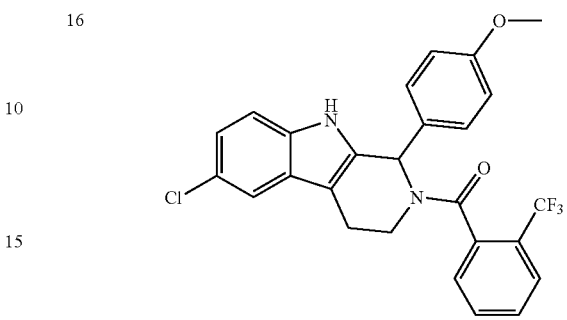 |
| 17 | 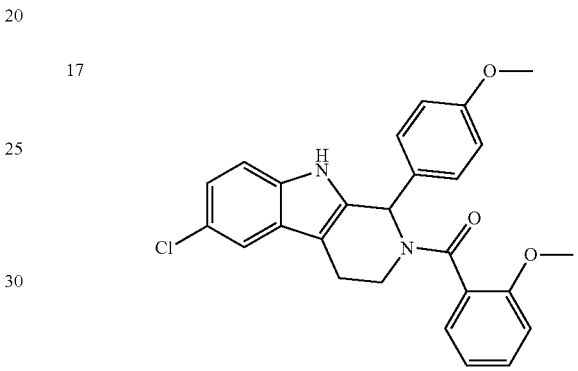 |
| 18 | 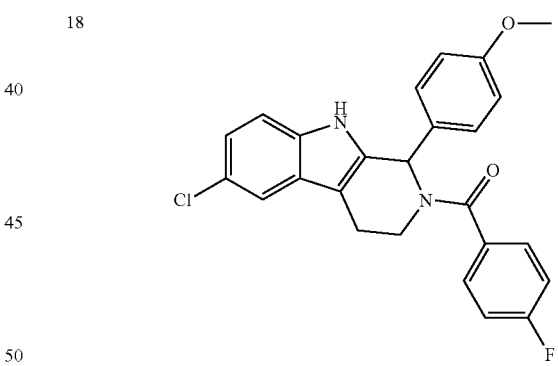 |
| 19 | 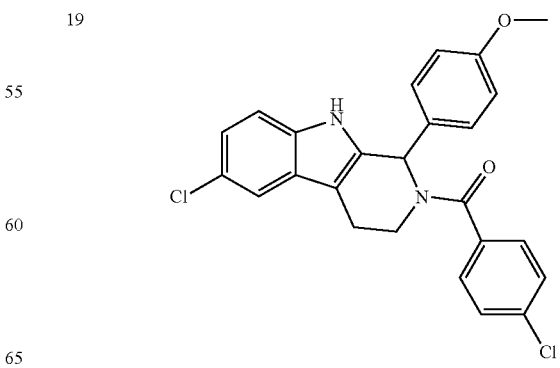 |

| Com- pound # | Compound Structure |
|---|---|
| 20 | 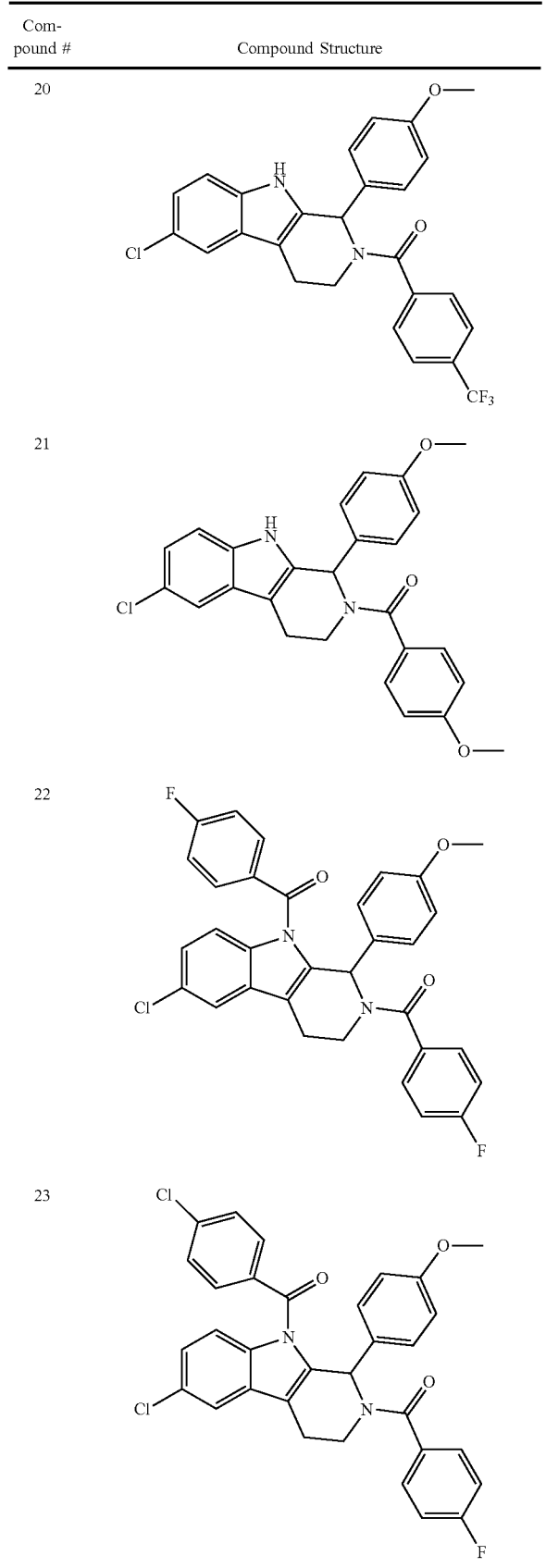 |
| 21 | 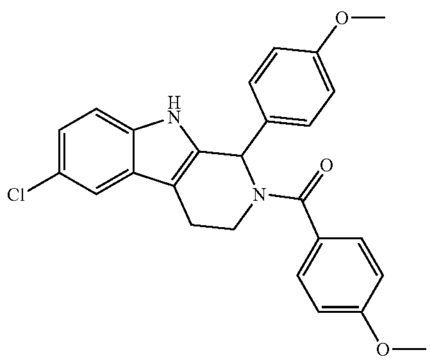 [SMILES: COc1ccc(C(=O)N2CCc3c([nH]c4ccc(Cl)cc34)C2c2ccc(OC)cc2)cc1] |
| 22 | 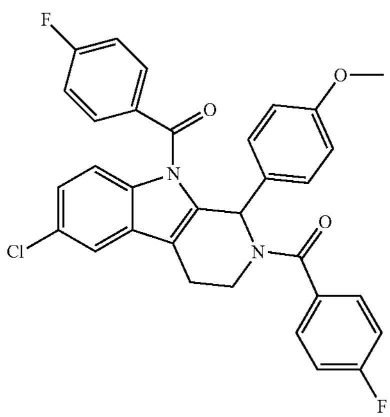 [SMILES: COc1ccc(C2c3c(c4cc(Cl)ccc4n3C(=O)c3ccc(F)cc3)CCN2C(=O)c2ccc(F)cc2)cc1] |
| 23 | 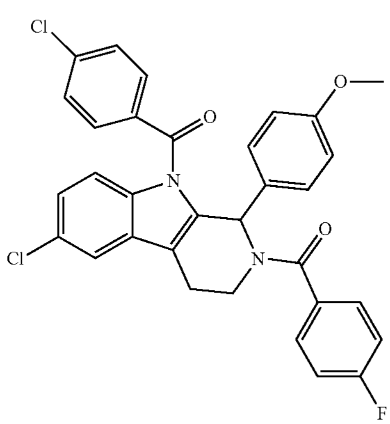 [SMILES: COc1ccc(C2c3c(c4cc(Cl)ccc4n3C(=O)c3ccc(Cl)cc3)CCN2C(=O)c2ccc(F)cc2)cc1] |

| Com- pound # | Compound Structure |
|---|---|
| 24 | 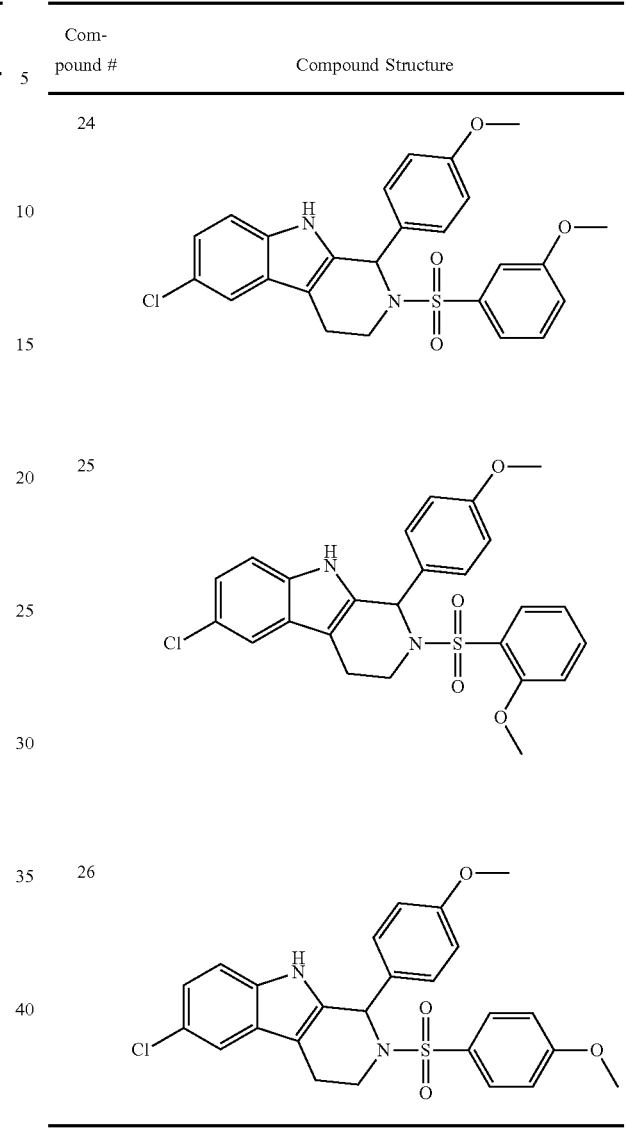 |
| 25 | 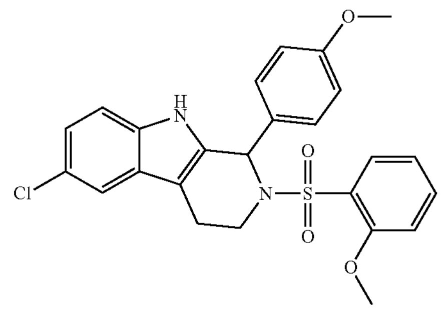 [SMILES: COc1ccc(C2c3[nH]c4ccc(Cl)cc4c3CCN2S(=O)(=O)c2ccccc2OC)cc1] |
| 26 | 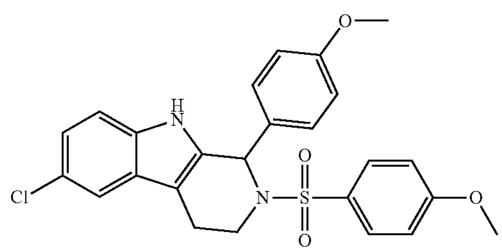 [SMILES: COc1ccc(C2c3[nH]c4ccc(Cl)cc4c3CCN2S(=O)(=O)c2ccc(OC)cc2)cc1] |

Compounds 10, 11, and 24-26 were found in the above-noted library. Compounds 9 and 12-21, i.e., the amides, were prepared as described in Scheme 1 using skill and reagents know to those in the art. In one embodiment, the first step of the reaction is performed in the presence of a strong acid such as 0.5M HCl at reflux for about 14 hours. In another embodiment, the second step of the reaction is performed in dichloromethane and diisopropylethylamine at room temperature.

Scheme 1

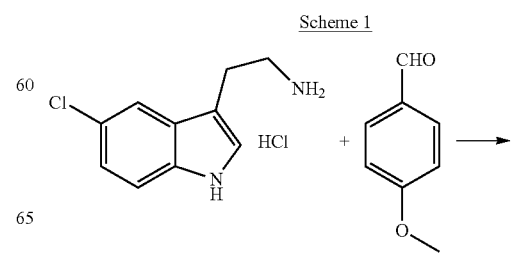

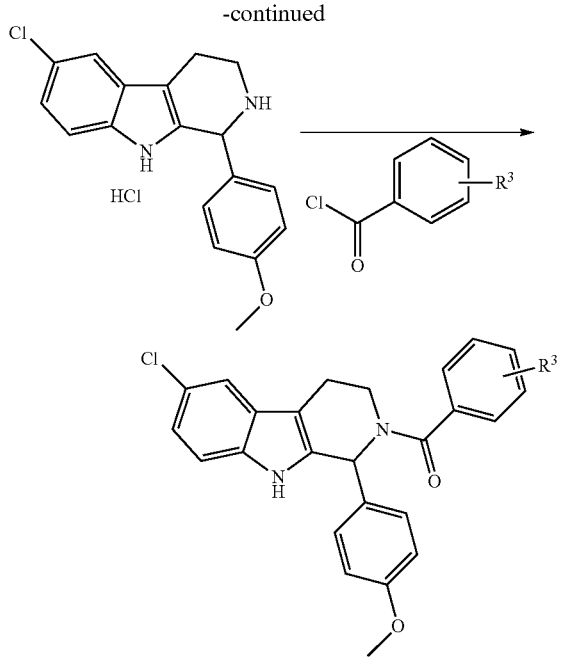

Compounds 22 and 23 were prepared by performing the amide using the above-noted scheme, followed by protection of the indole moiety according to Scheme 2. One skilled in the art would readily be able to use skill and reagents know in the art to perform such a reaction.

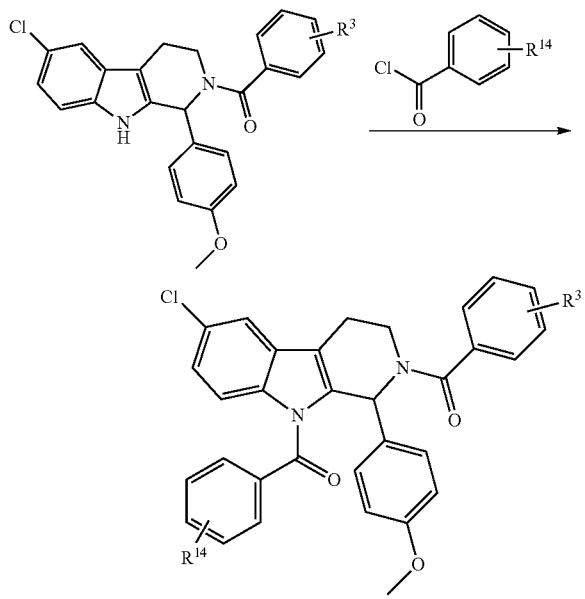

Figure 3:
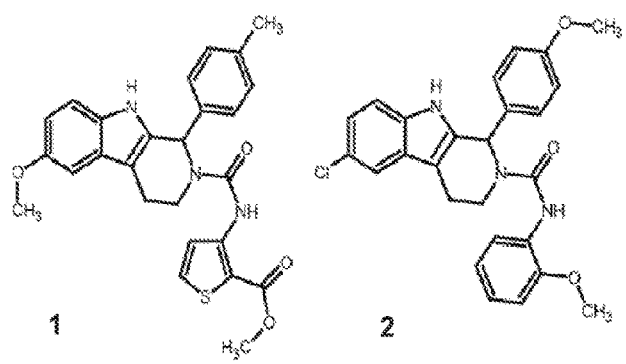
FIGS. 3A-3F shows the $EC_{50}$ analysis of compounds 1-5 discussed herein which are activators of EBV. Specifically.
Figure 3:
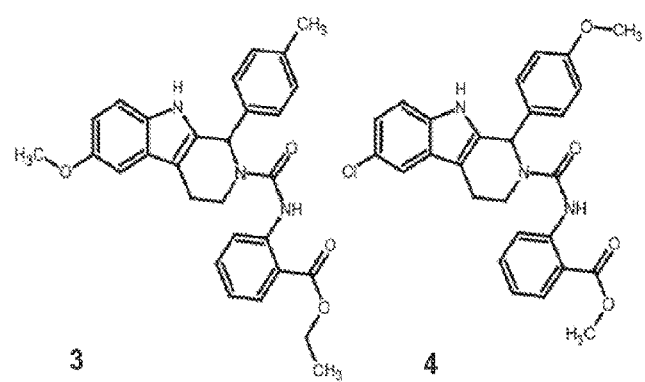
Figure 3:
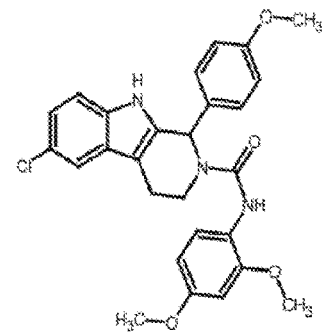
Figure 3:
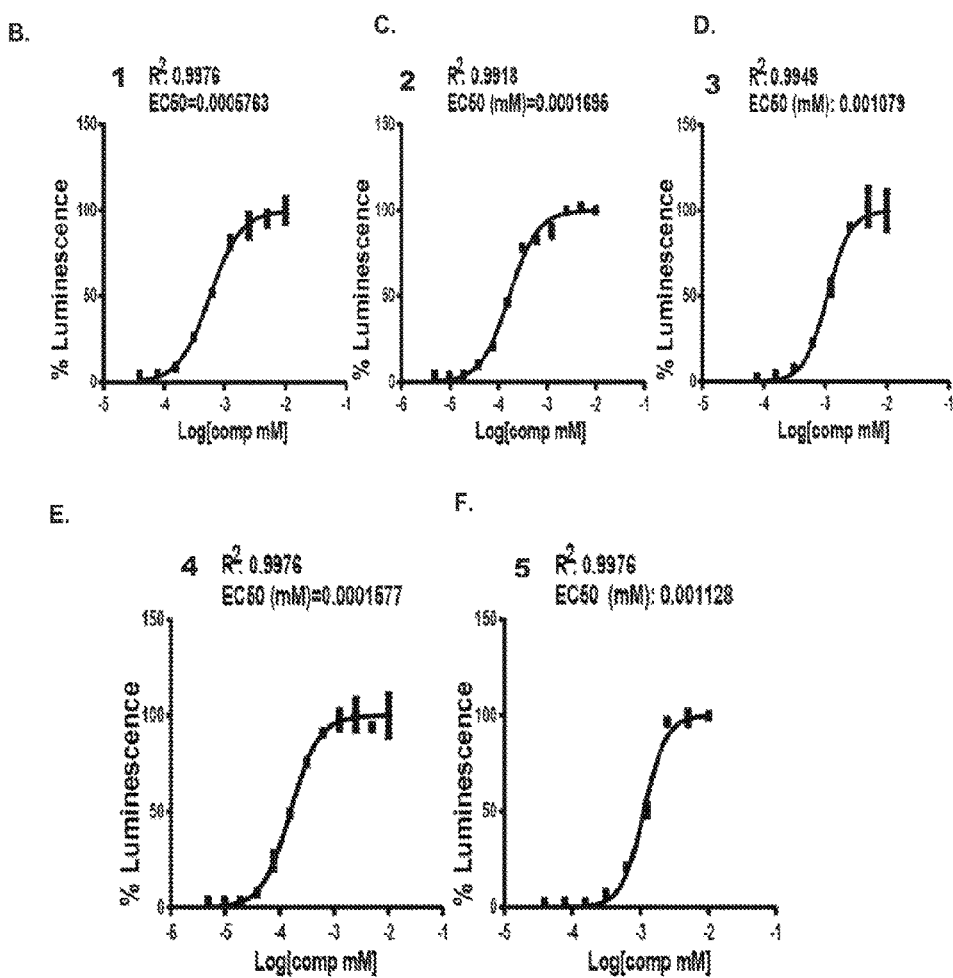

To further characterize the activity of these molecules 1-5, 10-23, 25, and 26, the concentration-dependent response of each compound's activity was assessed. As shown in FIG. 3, compounds 1-5 displayed concentration-dependent responses with $EC_{50}$ values that range between 160 nM to 1 μM. Compounds 10-26 had the $EC_{50}$ values set forth in Table B. Compounds 2, 4, 10, 12, 21, and 22 were the most potent activators, with $EC_{50}$ values at about 50 to about 200 nM. In contrast, NaB and arginine butyrate typically required millimolar concentrations to trigger the latent to lytic switch (Ghosh, 2012, Blood 119:1008-1017; Countryman, 2009, J. Virol. 83:10694-10709; and Miller, 2007, Adv. Cancer Res. 97:81-109) (FIG. 1B).

TABLE B

| Compound # | $EC_{50}$ (nM) |
|---|---|
| 10 | A |
| 11 | A |
| 12 | A |
| 13 | B |
| 14 | B |
| 15 | B |
| 16 | B |
| 17 | B |
| 18 | B |
| 19 | A |
| 20 | A |
| 21 | A |
| 22 | A |
| 23 | B |
| 25 | B |
| 26 | B |

* A is an $EC_{50}$ <500 nM B is an $EC_{50}$ >500 nM

Most chemical activators of EBV lytic gene expression trigger reactivation in only a small proportion (up to 30%) of the cell population (Miller, 2007, Adv. Cancer Res. 97:81-109; Daigle, 2011, J. Virol. 85:5628-5643; and Daigle, 2010, J. Virol. 84:993-1004). Triggering lytic reactivation in a higher percentage of refractory cells was an important goal for EBV lytic therapy. To determine the percentage of Mutul and LCL cells reactivated with the newly identified compounds, a Mutul-Hp-GFP stable cell line was generated to monitor lytic reactivation using fluorescence activated flow cytometry. Immunostaining for viral capsid antigen (VCA) was also used to confirm the findings.

Figure 2:
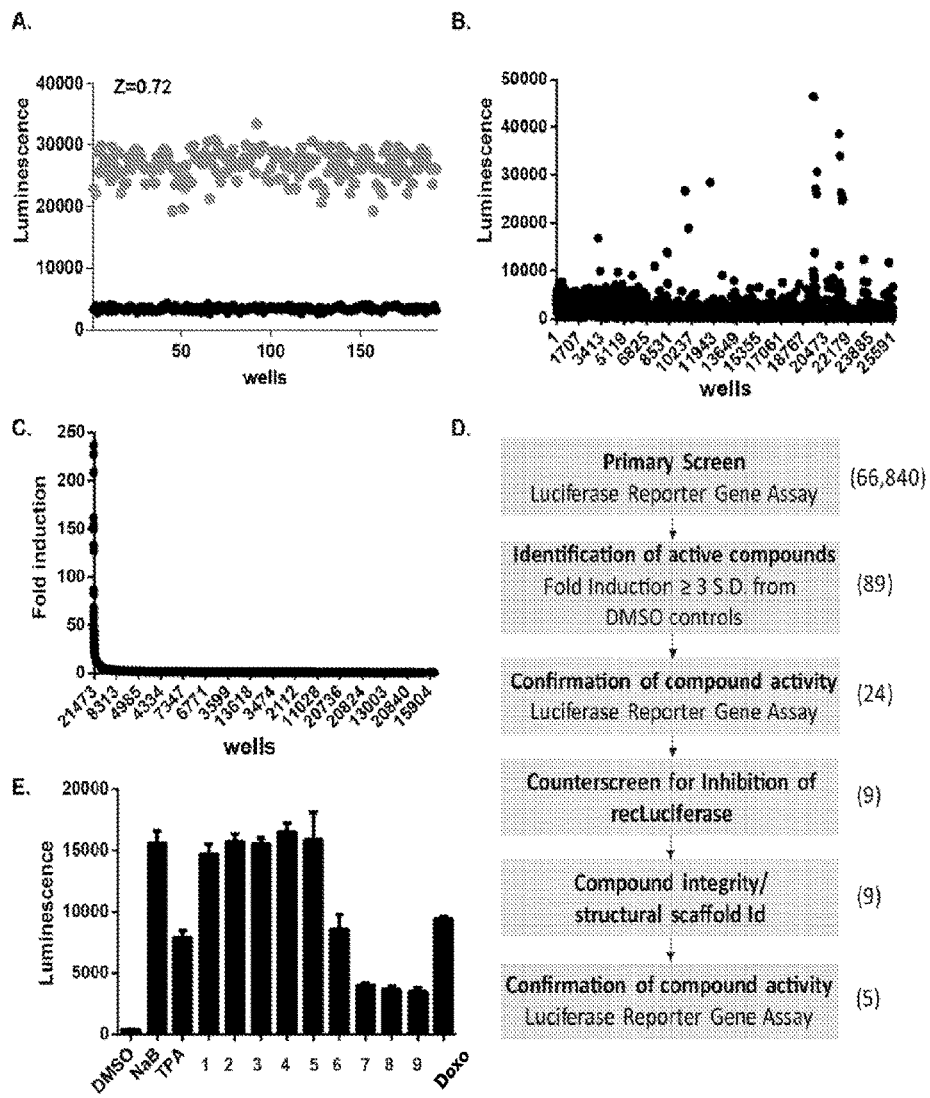
FIGS. 2A-2E illustrate the high-throughput screen (HTS) validation and results.
Figure 5:
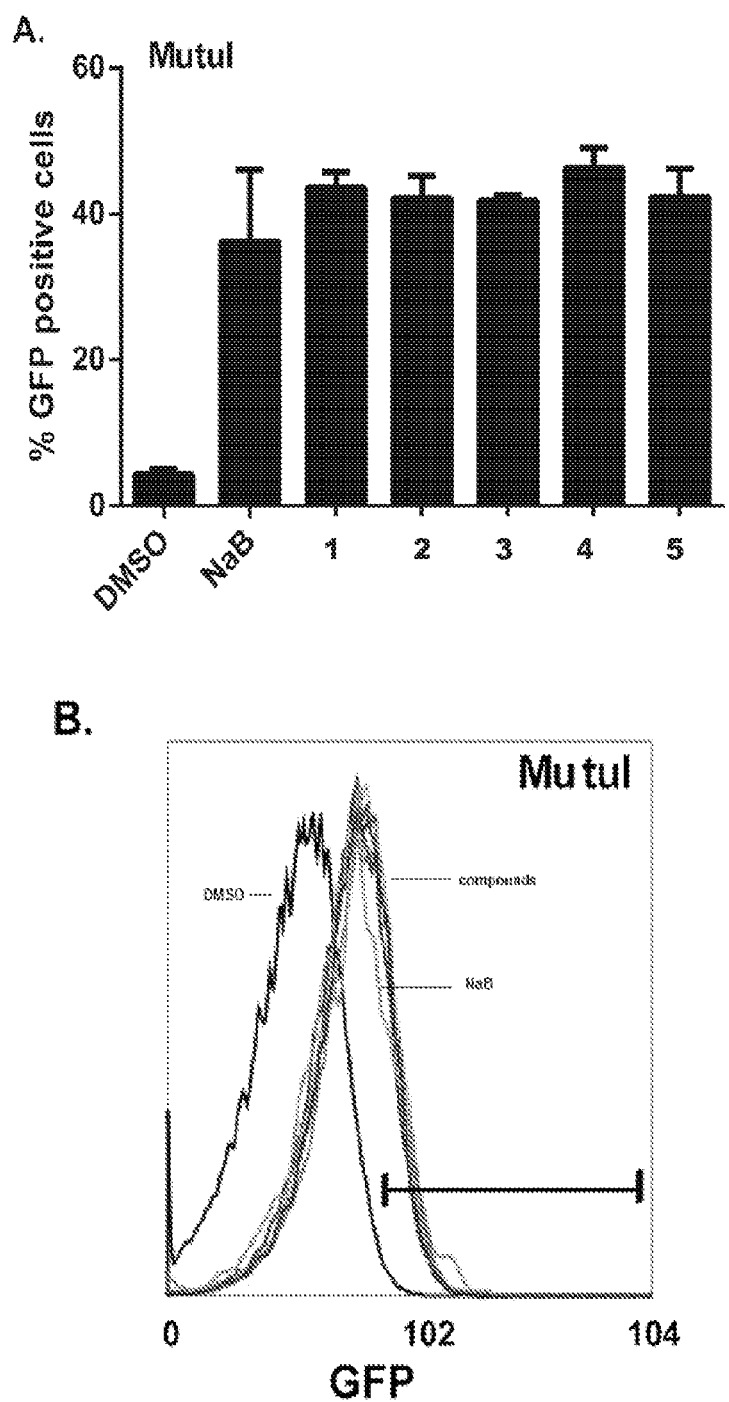
FIGS. 5A-D illustrates the percentage of lytic cells induced by compounds 1-5 described herein.
Figure 5:
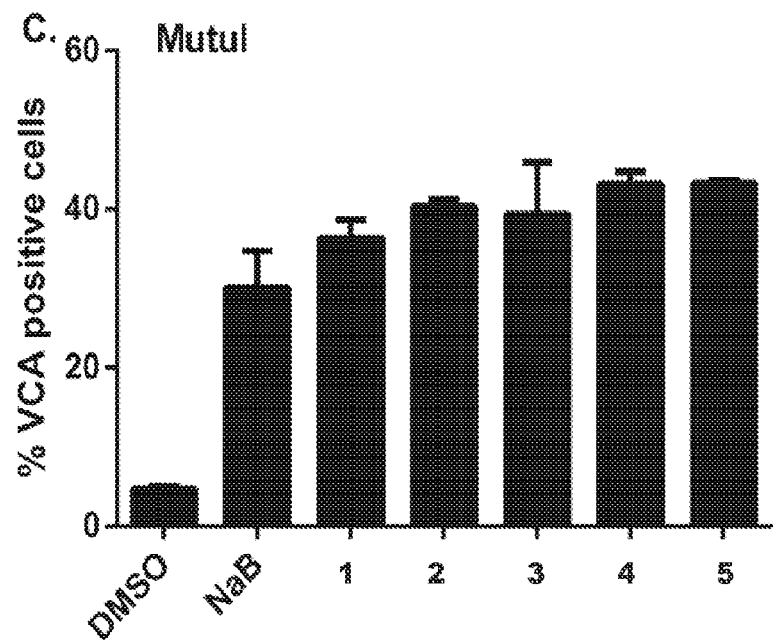
Figure 5:
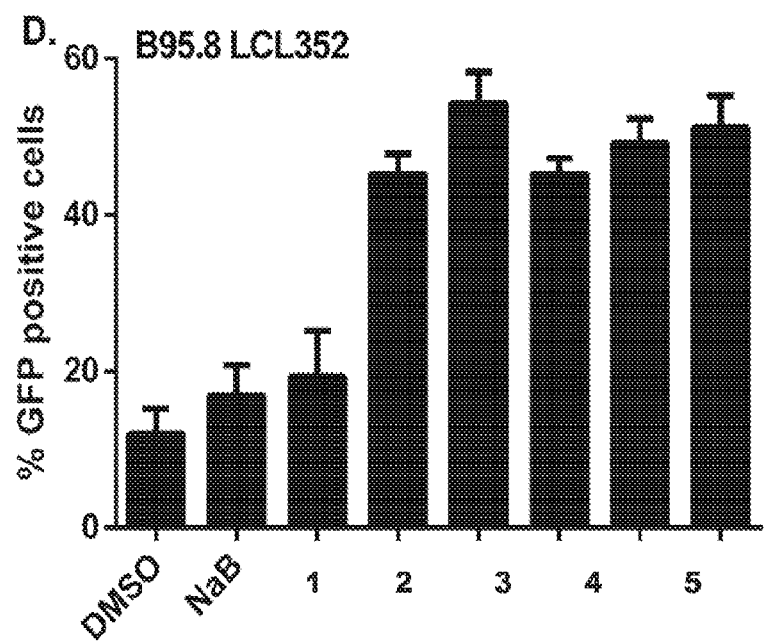

Out of small molecule EBV activators 1-5, compound 4 was consistently a well-performing EBV lytic cycle inducer in all cell lines tested. Titration of compound 4 (FIG. 5) with GCV showed that compound 4 synergizes with GCV on killing EBV-positive cells only at concentrations that cause EBV reactivation (FIG. 2). Furthermore, this cytotoxic synergy was not observed in EBV-negative cells. In contrast to NaB, all of compounds 1-5 did not produce cell toxicity in EBV negative cells. This selectivity offers possibility for further investigation of in vivo efficacy and toxicity of these compounds. It was found that 40-50% of Mutul-Hp-GFP cells expressed GFP after 72 h of treatment with these compound reactivators (FIGS. 5A and 5B), and a comparable percentage of Mutul cells expressed VCA on their surface after a 96-h treatment (FIG. 5C). Treatment of B95-8-infected LCLs that carry a GFP-EBV genome with these activators induced greater than 50% of the cells to become lytic after a 72-h treatment (FIG. 5D). In all cases, the newly identified compounds induced lytic activation in an equal or greater percentage of cells compared to treatment with 2 mM NaB.

EXAMPLE 3

Structure Studies

All EBV activators 1-26 share similar structure belonging to the tetrahydrocarboline structural class of compounds. Tetrahydrocarbolines are an interesting class of molecules that are known to possess diverse biological activity such as kinesin spindle protein, topoisomerase II, protein tyrosine phosphatase, phosphodiesterase inhibition, and sst3 receptor antagonists (Pasternak, 2012, ACS Med. Chem. Lett. 3:289-293 and Daugan, 2003, J. Med. Chem., 46:4525-4532). The active molecules 1-5 provide some initial structure activity relationships (SAR) required for EBV reactivation. All five have substitution on the 6 position of the indole ring with either a chloro or a methoxy group. Also all five are linked through the piperidine nitrogen with a urea linkage terminating with a substituted aromatic ring. The initial lead chemical series was chemically tractable and readily amenable to analog synthesis to flesh out the SAR to improve potency and drug-like properties of this novel class of EBV reactivators.

EXAMPLE 4

Combination Studies

Combining agents that induce the lytic cycle of EBV with inhibitors of viral lytic replication has been shown to be a promising strategy to eliminate EBV-positive cancers (Perrine, Blood 109:2571-2578; and Ghosh, 2012, Blood 119: 1008-1017).

Figure 6:
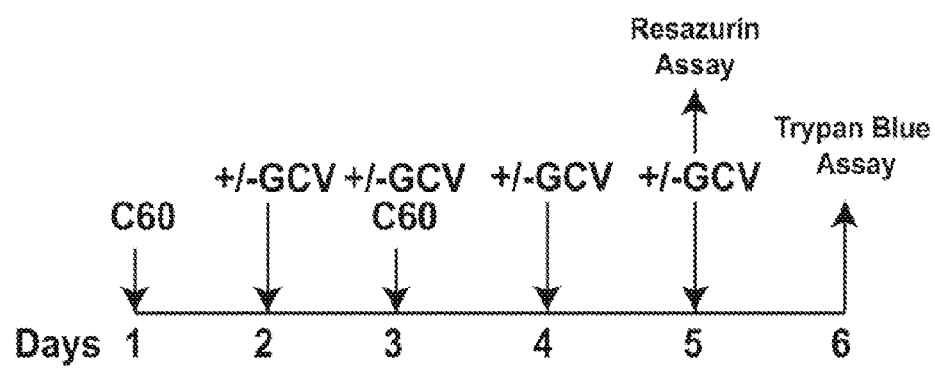
FIGS. 6A-J illustrate the synergizing effect of EBV activator Compound 4 and GCV in inducing apoptosis in EBV-positive cells.
Figure 6:
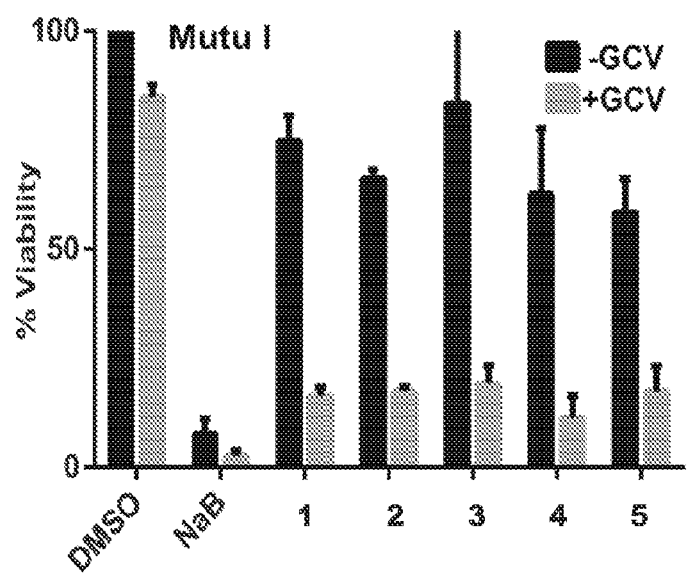
Figure 6:
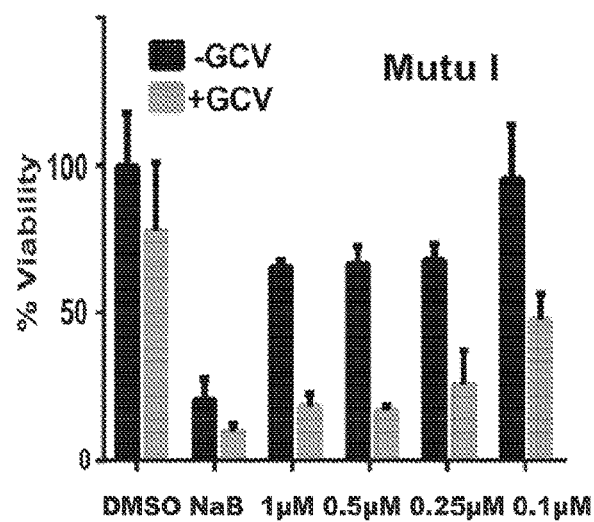
Figure 6:
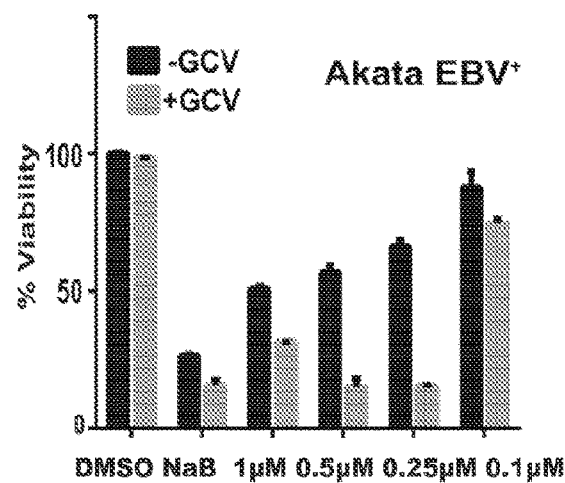
Figure 6:
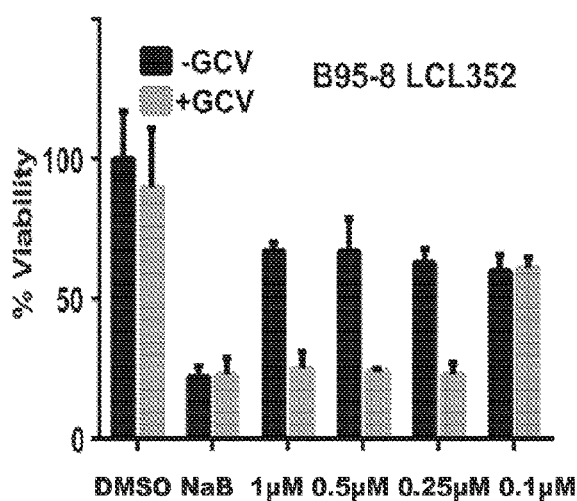
Figure 6:
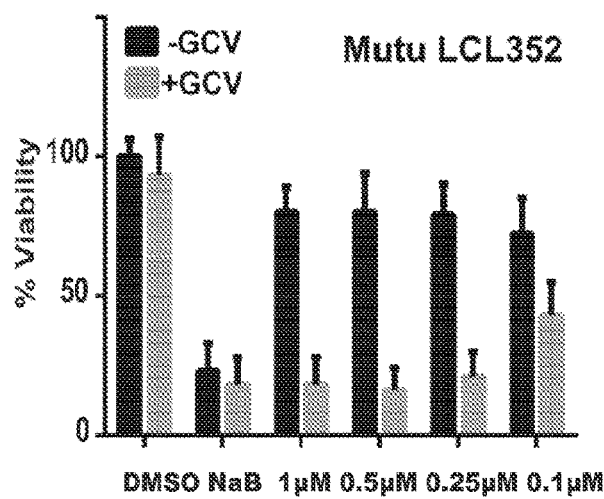
Figure 6:
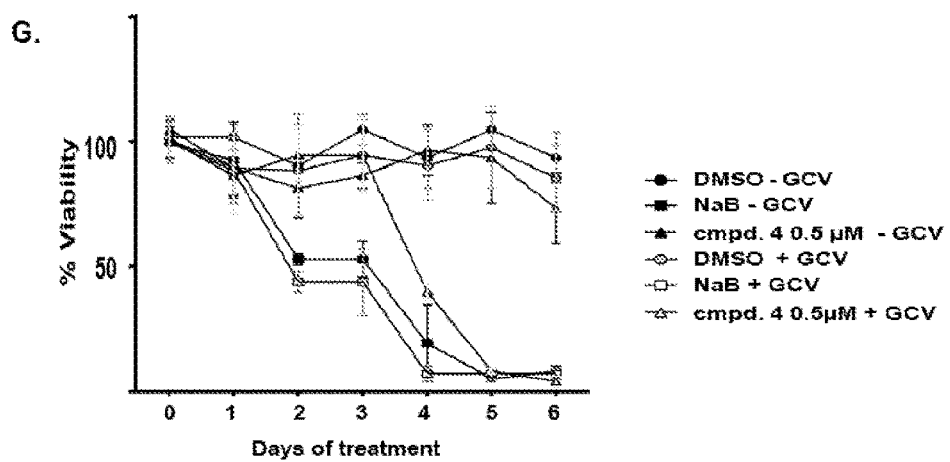
Figure 6:
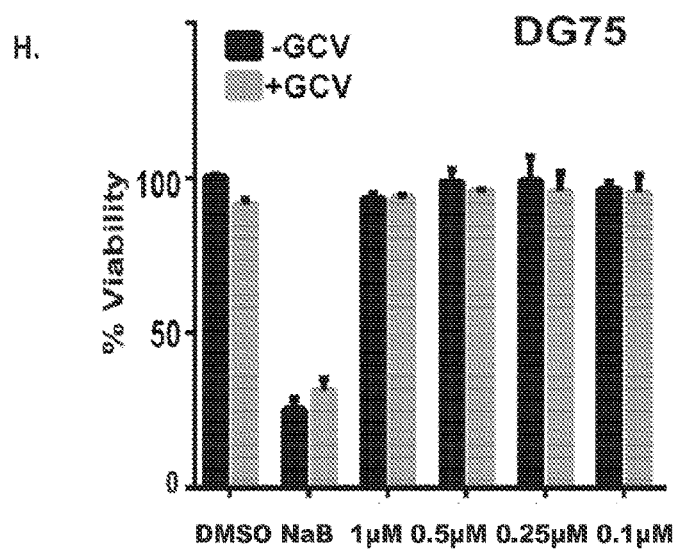
Figure 6:
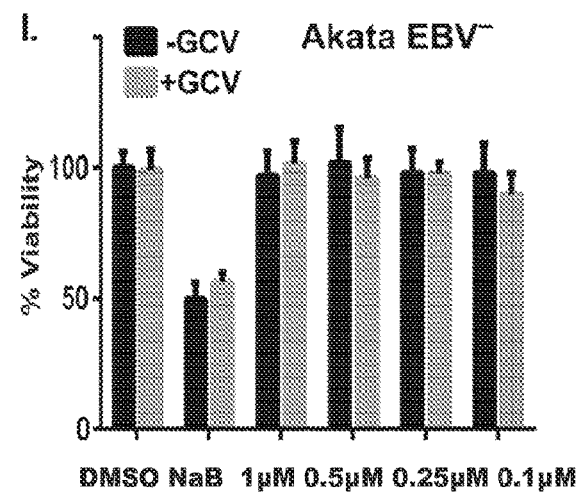
Figure 6:
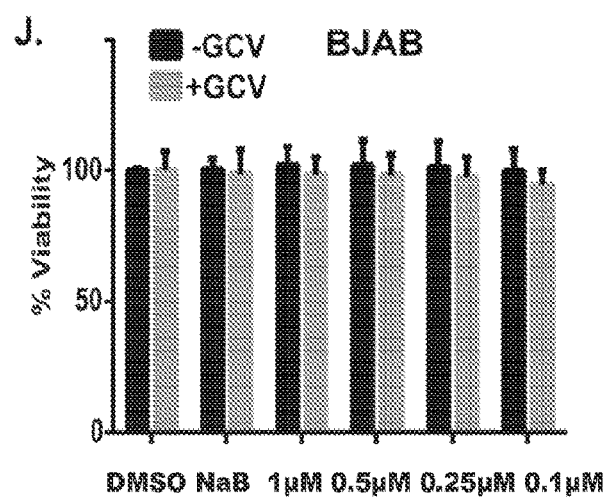

It was tested whether combination of the newly identified reactivators and GCV would increase selective cell killing of EBV infected cells. The experimental design is described in FIG. 6A. Specifically, gangcyclovir (GCV) was combined with a sublethal dose of compounds (1 µM) to determine if it could induce cell death in Mutul cells after six days of treatment. Cell viability was measured by trypan blue dye exclusion. As a single agent GCV reduced Mutul cell viability by ~10% over the course of 6 days. Treatment of Mutul cells with 1 µM of the newly identified activators as single agents reduced the viability of cultures by 15 to 30%, possibly due to the fact that EBV reactivation itself reduces host cell viability. The combination of compounds with GCV produced a synergistic effect killing nearly 80% of Mutul cells within 6 days. (FIG. 6B).

Figure 4:
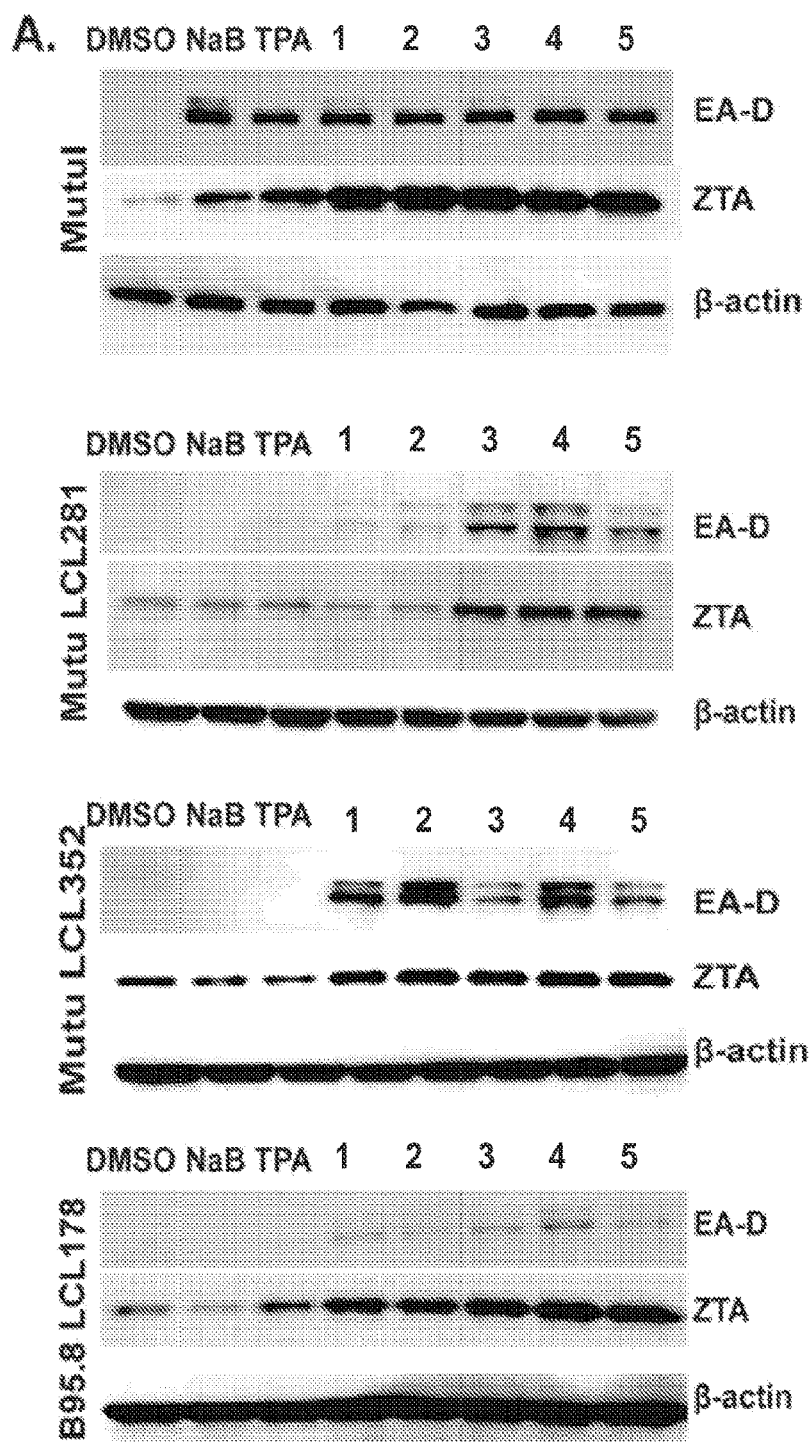
FIGS. 4A-E illustrates that various latency types are switched to lytic cycle by compounds 1-5 described herein.
Figure 4:
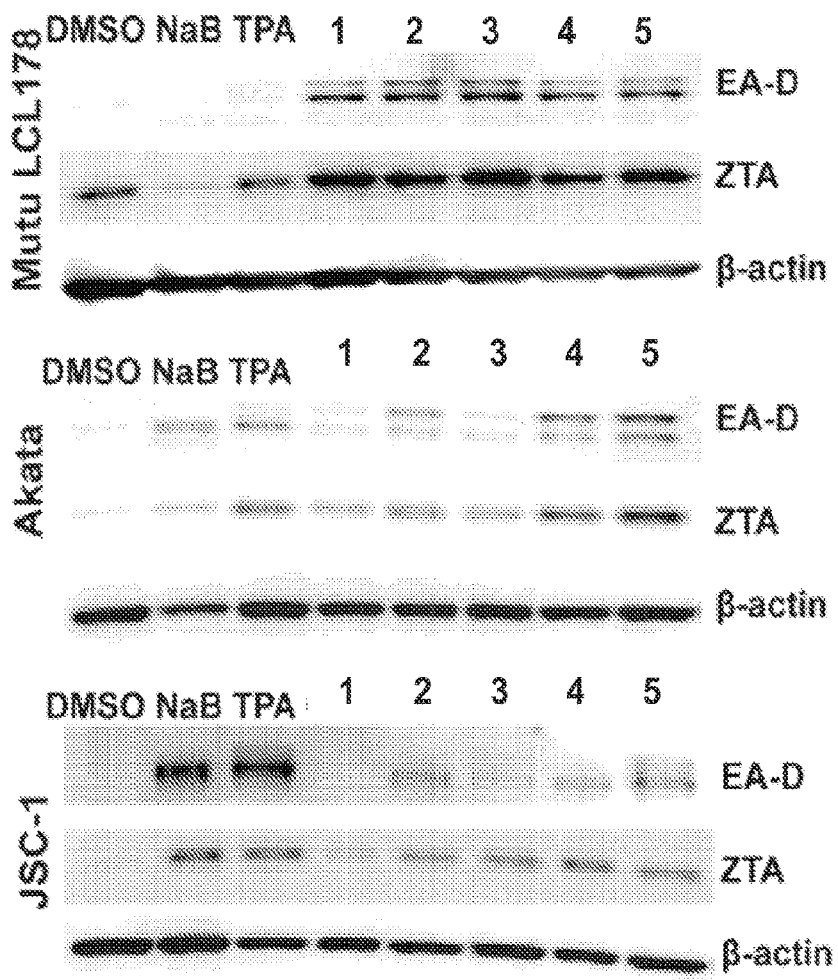
Figure 4:
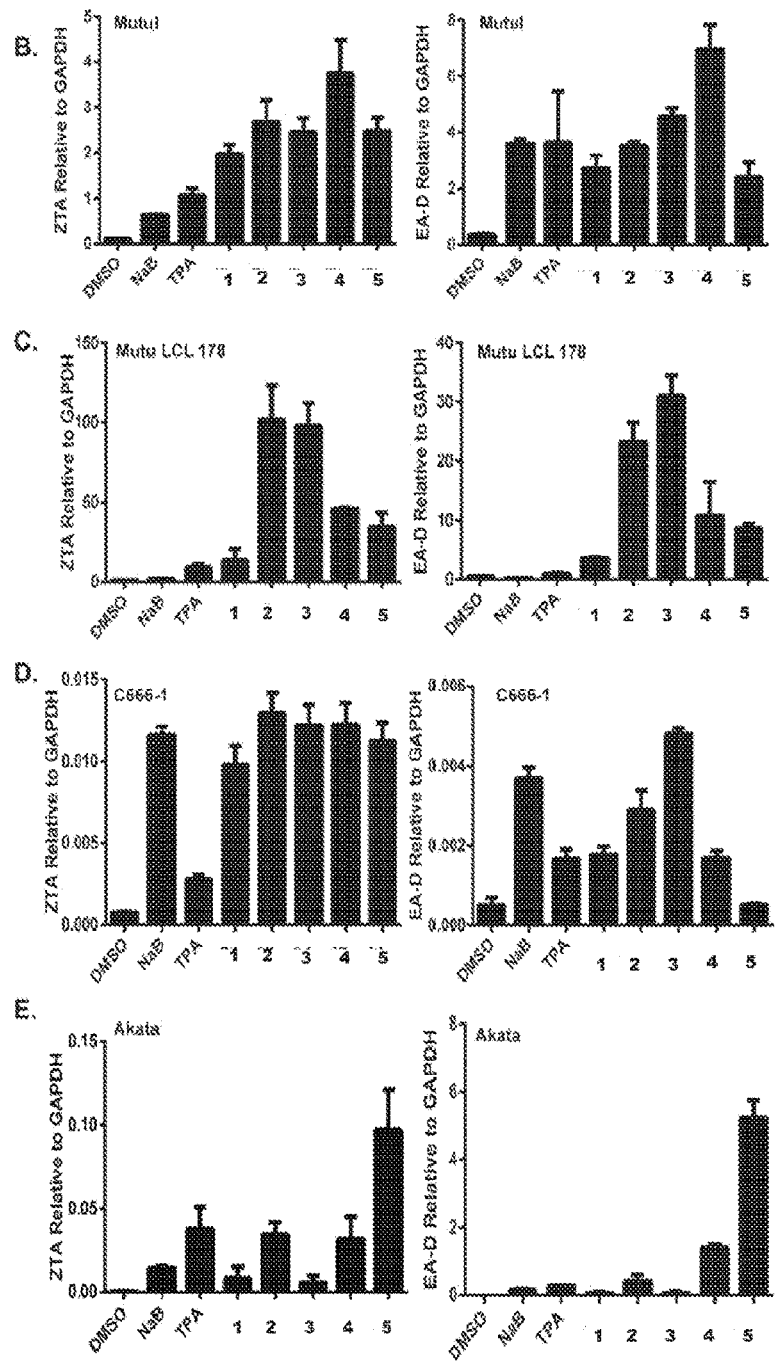

We compared a variety of cell lines with different latency types to determine whether the newly identified compounds are only active in Mutul or can be used to initiate lytic expression in other cells (FIG. 4). Compounds 1-5 were compared with positive controls NaB or TPA, relative to DMSO negative control. EBV lytic antigens EA-D and ZTA expression by Western blot for Mutu I (Type I BL), various LCLs (Type III LCL), Akata (Type I BL cell), and JSC1 (KSHV co-infected PEL cell) were assayed. Also assayed were EA-D (BMRF1 gene) and Zta (BZLF1 gene) expression by RT-PCR for Mutul, Mutu-LCL, C666-1 (Type II NPC cells), and Akata cells (FIGS. 4B-E). For all cell lines tested, the new compounds were able to upregulate expression of EA-D and ZTA. In several cases, the compounds stimulated EA-D and ZTA to levels equal to or greater than 2 mM NaB treatment. This indicated that these compounds have a broad tropism for activation of EBV lytic cycle gene expression.

Compound 4 was selected for dilution studies since it showed the greatest potency in Mutul cell based assays (FIG. 3), and consistently stimulated EBV lytic reactivation in multiple cell types (FIG. 4). Mutul, Akata, and OG75 cells were treated with a range of compound 4 concentrations either as a single agent or in combination with 10 µg/mL of GCV according to the scheme (FIG. 6A). For these experiments, a fluorescence-based readout (resazurin/Alomar blue) assay was utilized as the indicator of cell viability. Synergistic cell killing was observed for EBV positive Mutul (FIG. 6C) and Akata cells (FIG. 6D). In contrast, compound 4 produced no observable effect on the viability of a EBV negative BL cell line OG75, either as a single agent or in combination with GCV (FIG. 6C, right panel). The scheme in FIG. 6A was followed to address whether the addition of GCV to either compound 4 or NaB kills Mutul cells in a time-dependent manner. Daily measurements of the viability of Mutul cells treated with DMSO, NaB, or 0.5 µM of compound 4 were measured with or without GCV using resazurin (FIG. 6G). The synergistic effects of compound 4 with GCV could be observed by day 4. In contrast, NaB did not synergize with GCV, since it was toxic to cells regardless of EBV positive status, possibly due to its broad function as HDAC inhibitor, and stimulation of many genes unrelated to EBV function (FIG. 6G).

EXAMPLE 5

Mechanism of Action

Butyrates are known inhibitors of HOACs (Marks, 2004, Novartis Foundation symposium 259:269-281; discussion 281-268). The mechanism of TPA reactivation of EBV has also been studied in depth (Nakagawa, 2012, Biosci., Biotechnol., and Biochem., 76:1262-1274; and Gao, 2001, Virology 286:91-99). TPA first activates PKC and within 30 minutes triggers p38MAPK kinase phosphorylation (Griner, 2007, Nature Rev. Cancer 7:281-294), resulting in upregulation of MAPK pathway. Through activation of Erk1/2, TPA is also known to phosphorylate p53 and ribosomal kinases, such as p90RSK and S6 (Griner, 2007, Nature Rev., 7:281-294).

Figure 7:
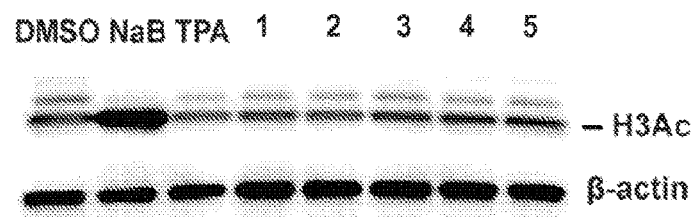
FIGS. 7A-C are gels illustrating the mechanism of EBV reactivation of the compounds in distinct from HDAC inhibitors and TPA.
Figure 7:
Figure 7:
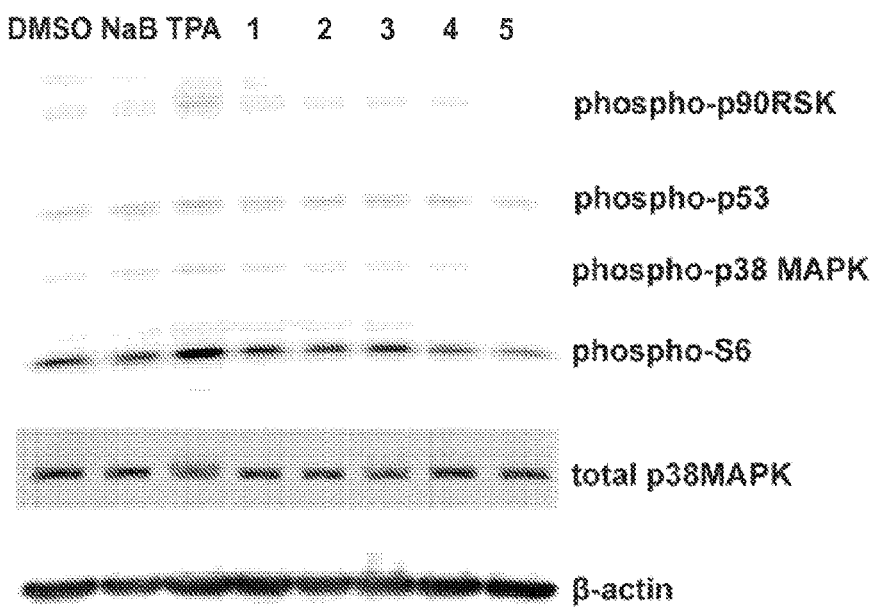

Mutul and Mutu-LCL352 cell lines were used to test whether the newly identified EBV activators function as HDACs by increasing acetylation on histone H3. While NaB caused histone acetylation in both cell lines as expected, none of the EBV activators stimulated H3 acetylation, indicating they do not function as HDACs, like NaB (FIGS. 7A and 7B).

To test whether the newly identified compounds share the mechanism of EBV reactivation with TPA, an antibody cocktail was used to detect p38 MAPK, S6, p90RSK and p53 phosphorylation. As expected, TPA showed an increase in phosphorylation of these kinases. In contrast, the compounds failed to induce detectable levels of phosphorylation of these targets, suggesting that the mechanisms of EBV activation by the newly identified compounds have a mechanism distinct from TPA (FIG. 7C).

The data suggests that the identified compounds' mechanisms of action are distinct from those already known came from the observation that the new compounds are able to reactivate EBV even in Mutu and B95.8 LCL cell lines resistant to NaB or TPA. Checking histone H3 acetylation and the activity of p38 MAPK signaling cascade indicated that the new EBV activators are unlikely to be HDAC inhibitors, like NaB, nor stimulate the cellular signaling pathways commonly activated by TPA.

The new compounds have improved cell tropism and increase frequency of activation relative to standard reactivating reagents, NaB and TPA. Compound 4 and its analogues can induce lytic activation in a wide variety of EBV positive cells, including BLs, LCLs, PELs, and NPC derived cell lines. It was also found that these newly identified compounds can induce nearly 50% of Mutu I and over 50% of LCL cell—the highest percentage that has been achieved to date for chemical reactivation methods.

Out of the novel small molecule EBV activators 1-5, compound 4 was consistently a well-performing EBV lytic cycle inducer in all cell lines tested. Titration of compound 4 (FIG. 5) with GCV showed that compound 4 synergized with GCV on killing EBV-positive cells only at concentrations that cause EBV reactivation (FIG. 2). Furthermore, this cytotoxic synergy was not observed in EBV-negative cells. In contrast to NaB, all five compounds did not produce cell toxicity in EBV negative cells.

In conclusion, the compounds identified through use of this assay can activate EBV from a wide range of latently infected lymphoid and epithelial derived tumor cells. These newly identified reactivators can improve therapeutic approaches for EBV specific oncolytic therapies.

EXAMPLE 6

Augmentation of ZTA-dependent Transcription Activiation of Viral Early Promoters To test whether the class of new compounds act by transcription activation of ZTA(Zp), RTA(Rp), or BHLF1 (Hp) promoter, 293T cells were transfected with plasmids containing Zp, Rp, or Hp promoter regions controlling luciferase reporter and treated with either DMSO or 1 µM of compound 4 (FIGS. 9A-9C). Compound 4 alone produced an about 4-fold activation of Zp and Rp (FIGS. 9A-B) but had slight inhibitory effect on Hp 310 (FIG. 9C). To test whether compound 4 enhanced ZTA- or RTA- dependent activation, cells were co-transfected with ZTA or RTA and then treated with either DMSO or 1 µM of compound 4.

Figure 9:
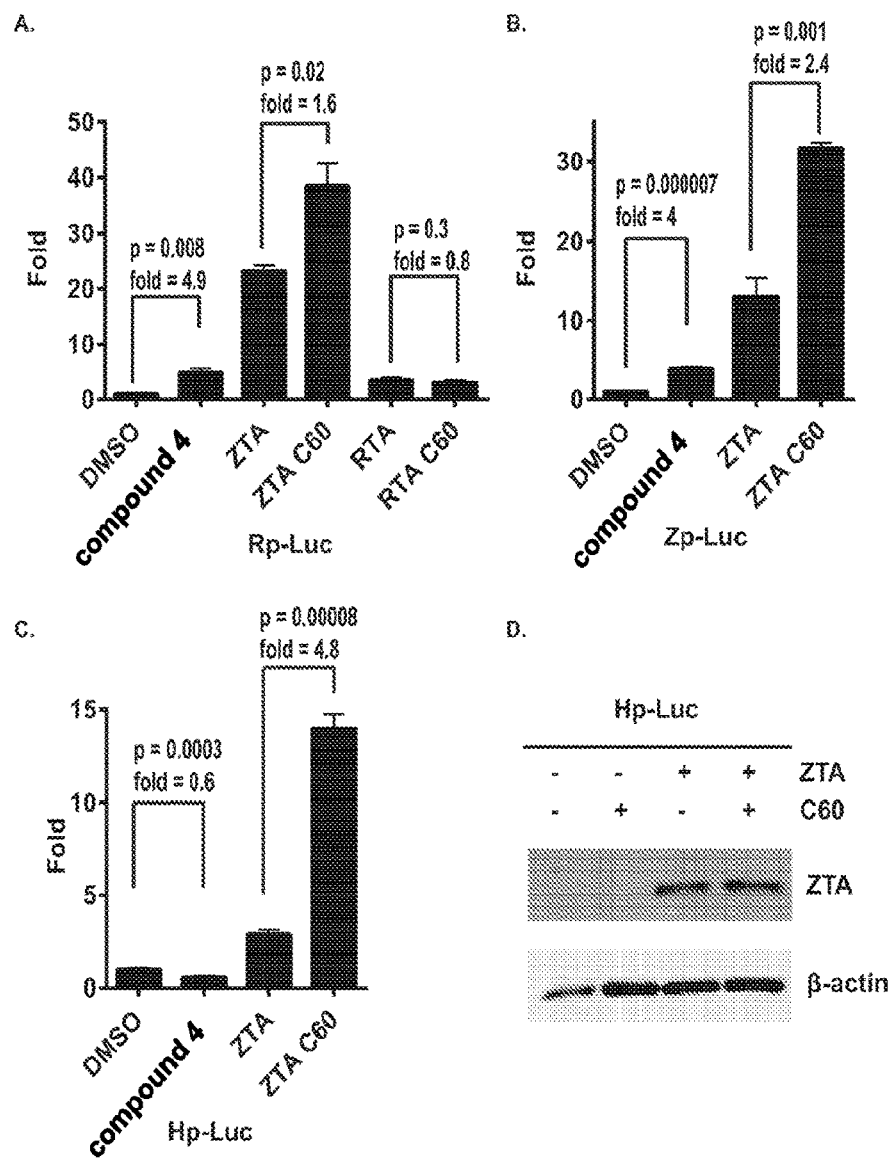
FIGS. 9A-9D illustrate the stimulating effect on the transcription of the EBV immediate early gene promoters Zp and Rp (FIGS. 9A-9C) and the augmenting effects on ZTA transcription activation (FIG. 9D).

It was found that compound 4 was capable of stimulating transcription of the EBV immediate early gene promoters Zp and Rp, as well as augmenting ZTA transcription activation (FIG. 9). Specifically, compound 4 augmented ZTA activation on all three promoters, increasing the luciferase signal 4.8-fold in Hp-Luc cells, 2.4-fold in Zp-Luc, and 1.6-fold in Rp-Luc cells (FIGS. 9A-C). In contrast, compound 4 had no effect on RTA activation of Rp (FIG. 9A). Compound 4 did not increase ZTA protein levels or mobility as indicated by Western blot analysis of transfected cells (FIG. 9D).

These findings suggested that compound 4 functions through a pathway that regulates transcription control of viral immediate early promoters and the ZTA transcriptional activator.

All publications cited in this specification and priority application, including U.S. Provisional Patent Application No. 61/872,673, filed Aug. 31, 2013, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method for reactivating latent Epstein-Barr virus (EBV) in a cell, said method comprising administering a compound of the formula to a subject in need thereof:

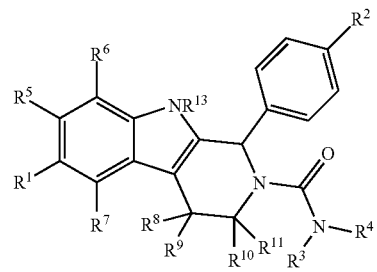

wherein:
$R^1$ is H, $C_1$ to $C_6$ alkyl, $C_1$ to $C_6$ alkoxy, or halogen;
$R^2$ is H, $C_1$ to $C_6$ alkyl, or $C_1$ to $C_6$ alkoxy;
$R^3$ is a phenyl group substituted on the C in its second position with $-C(O)OCH_3$;
$R^4$ is H or optionally substituted $C_1$ to $C_6$ alkyl;
$R^5$ to $R^{11}$ are, independently, selected from the group consisting of H and $C_1$ to $C_6$ alkyl; and
$R^{13}$ is H, optionally substituted aryl, or optionally substituted heteroaryl; or a pharmaceutically acceptable acid salt or base salt or prodrug thereof.

2. The method according to claim 1, further comprising administering a histone deacetylase inhibitor or a proteasome inhibitor.

3. The method according to claim 2, wherein said histone deactylase inhibitor is arginine butyrate, or sodium butyrate or is suerboylanilide hydroxamic acid (SAHA).

4. The method according to claim 1, wherein said method (a) prevents or treats EBV-positive cancer, or (b) prevents post-transplant lymphoproliferative disease when said subject is immunosuppressed.

5. The method according to claim 4, further comprising administering an anti-viral agent or a chemotherapeutic or administering radiation to said subject.

6. The method according to claim 5, wherein said anti-viral agent or chemotherapeutic or radiation is administered prior to, concurrently with, or subsequent to administration of said compound.

7. The method according to claim 1, wherein $R^1$ is $C_1$ to $C_6$ alkoxy or halogen.

8. The method according to claim 7, wherein $R^1$ is methoxy or chlorine.

9. The method according to claim 1, wherein said compound is

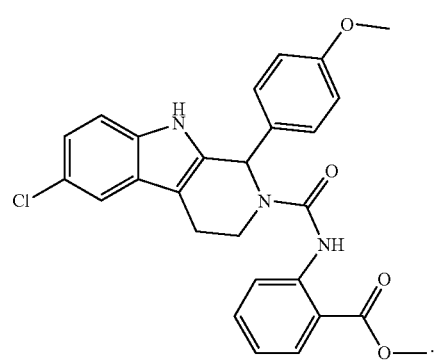 [SMILES: COC(=O)c1ccccc1NC(=O)N1CCc2c([nH]c3ccc(Cl)cc23)C1c1ccc(OC)cc1]

10. The method according to claim 1, wherein $R^2$ is $C_1$ to $C_6$ alkyl or $C_1$ to $C_6$ alkoxy.

11. The method according to claim 10, wherein $R^2$ is methyl or methoxy.

12. The method according to claim 1, wherein $R^4$ is H, $R^5$ is H, $R^6$ is H, $R^7$ is H, $R^8$ is H, $R^9$ is H, $R^{10}$ is H, $R^{11}$ is H, or $R^{13}$ is H.

\* \* \* \* \*